US007112568B2

(12) United States Patent
Eisenberg et al.

(10) Patent No.: US 7,112,568 B2
(45) Date of Patent: Sep. 26, 2006

(54) ANTI-ALLERGIC COMPLEX MOLECULES

(75) Inventors: Ronit Eisenberg, Nes-Ziona (IL); Tamar Raz, Rosh Haayin (IL)

(73) Assignee: Ramot At Tel Aviv University Ltd., Tel-Aviv (IL)

( * ) Notice: Subject to any disclaimer, the term of this patent is extended or adjusted under 35 U.S.C. 154(b) by 0 days.

(21) Appl. No.: 10/465,826

(22) Filed: Jun. 20, 2003

(65) Prior Publication Data

US 2004/0137006 A1 Jul. 15, 2004

(51) Int. Cl.
*A61K 38/00* (2006.01)

(52) U.S. Cl. .................. 514/12; 530/300; 424/185.1
(58) Field of Classification Search .............. 514/12; 530/300, 350
See application file for complete search history.

(56) References Cited

U.S. PATENT DOCUMENTS 5,807,746 A * 9/1998 Lin et al. ................... 435/375

OTHER PUBLICATIONS

Aridor et al., "Exocytosis in Mast Cells by Basic Secretagogues: Evidence for Direct Activation of GTP–binding Proteins," Journal of Cell Biology, vol. 111, pp. 909–917 (1990).
Aridor et al., "Neomycin is a Potent Secretagogue of Mast Cells that Directly Activates a GTP–binding Protein Involved in Exocytosis," Journal of Cell Biology, vol. 111, pp. 2885–2891 (1990).
Aridor et al., "Activation of Exocytosis by the Heterotrimeric G Protein $G_{i3}$," Science, vol. 262, pp. 1569–1572 (1993).
Bienenstock et al., "Mast Cell Involvement in Various Inflammatory Processes," Am Rev Repir Dis 1987; 135:S5–S8.
Chahdi et al., "Substance P–related inhibitors of mast cell exocytosis act on G–proteins or on the cell surface," European Journal of Pharmacology, vol. 341, pp. 329–335 (1998).
Columbo et al., "Substance P Activates the Release of Histamine from Human Skin Mast Cells through a Pertussis Toxin–Sensitive and Protein Kinase C–Dependent Mechanism," Clinical Immunology and Immunopathology, vol. 81, No. 1, pp. 68–73 (1996).
Devillier et al., "Histamine Release and Local Responses of Rat and Human Skin to Substance P and Other Mammalian Tachykinins," Pharmacology, vol. 32, pp. 340–347 (1986).
Emadi–Khiav et al., "Human and rat cutaneous mast cells: involvement of a G protein in the response to peptidergic stimuli," European Journal of Pharmacology, vol. 272, pp. 97–102 (1995).

Ennis et al., "Some Studies on the Release of Histamine From Mast Cells Stimulated with Polylysine," Br. J Pharmac., vol. 70, pp. 329–334 (1980).
Foreman, "Neuropeptides and the pathogenesis of allergy," Allergy, vol. 42, pp. 1–11 (1987).
Foreman, "Substance P and Calcitonin Gene–Related Peptide: Effects of Mast Cells and in Human Skin," Int. Arch. Allergy Appl. Immunol., vol. 82, pp. 366–371 (1987).
Goldberg et al., "Cutaneous responses to histamine, compound 48/80, and codeine in patients with chronic renal failure," Annals of Allergy, vol. 67. pp. 525–528 (1991).
Gomperts et al., "Intracellular Mechanisms Regulating Exocytotic Secretion in Mast Cells," Int. Arch. Allergy Appl. Immunol., vol. 94, pp. 38–46 (1991).
Hawiger, "Cellular import of functional peptides to block intracellular signaling," Curr Opin Immunol., vol. 9, pp. 189–194 (1997).
Kivity et al., "The effect of food and exercise on the skin response to compound 48/80 in patients with food–associated exercise–induced urticaria–angioedema," J. Allergy Clin. Immunol., vol. 81, pp. 1155–1158 (1988).
Lichtenstein, "Allergy and the Immune System,", Scientific American, pp. 117–124 (1993).
Lin et al., "Inhibition of Nuclear Translocation of Transcription Factor NF–κB by a Synthetic Peptide Containing a Cell Membrane–permeable Motif and Nuclear Localization Sequence," Journal of Biological Chemistry, vol. 270, pp. 14255–14258 (1995).
Liu et al., "Identification of a functionally important sequence in the cytoplasmic tail of integrin $\beta_3$ by using cell–permeable peptide analogs," Proc. Natl. Acad. Sci. USA, vol. 93, pp. 11819–11824 (1996).
Mousli et al., "Peptidrgic pathway in human skin and rat peritoneal mast cell activation," Immunopharmacology, vol. 27, pp. 1–11 (1994).
Pearce et al., "Characteristics of Histamine Secetion Induced by Neuropeptides: Implications for the Relevance of Peptide–Mast Cell Interactions in Allergy and Inflammation," Int. Arch. Allergy Appl. Immunol., vol. 88, pp. 129–131 (1989).
Prochiantz, "Getting hydrophilic compounds into cells: lessons from homeopeptides," Curr Opin Neurobiology, vol. 6, pp. 629–634 (1996).
Rojas et al., "Controlling Epidermal Growth Factor (EGF-)–stimulated Ras Activation in Intact Cells by a Cell–permeable Peptide Mimicking Phosphorylated EGF Receptor," Journal of Biological Chemistry, vol. 271, pp. 27456–27461 (1996).

(Continued)

*Primary Examiner*—John Weber
*Assistant Examiner*—Anand Desai

(57) ABSTRACT

The present invention discloses novel anti-allergic complex molecules, and in particular, peptidic or peptidomimetic molecules, comprising a first part which is competent for cell penetration and a second part which is able to reduce or abolish mast cell degranulation, in particular to reduce or abolish allergy mediators, including histamine secretion from mast cells and protein kinase activation, wherein the first part is connected to the second part via a linker or a direct bond that creates a conformational constraint by forming a bend or turn.

44 Claims, 16 Drawing Sheets

OTHER PUBLICATIONS

Sagi–Eisenberg, "Signal–Transmission Pathways in Mast Cell Exocytosis," Immunopharmacology of Mast Cells and Basophils, Academic Press Limited (1993), pp. 71–78.

Sagi–Eisenberg et al., "Structure–Activity Relationship in the Mast Cell Degranulating Capacity of Neurotensin Fragments," Neuropharmacology, vol. 22, pp. 197–201 (1983).

Shefler et al., "Basic secretagogues activate protein tyrosine phosphorylation and release of arachidonic acid in mast cells via a novel protein kinase C and phosphatidylinositol 3–kinase–dependent mechanism," Eur. J. Immunol., vol. 28, pp. 3468–3478 (1998).

Sussman et al., "Evaluation of Skin Test Response Using Two Techniques of Measurement," Annals of Allergy, vol. 48, pp. 75–77 (1982).

Theoharides, "The Mast Cell: A Neuroimmunoendocrine Master Player," Int. J. Tiss. Reac. XVIII(1), pp. 1–21 (1996).

* cited by examiner

Pep Concentration (μg/ml)

Pep Concentration (μg/ml)

ANTI-ALLERGIC COMPLEX MOLECULES

FIELD OF THE INVENTION

The present invention discloses novel anti-allergic complex molecules, and in particular, peptidic or peptidomimetic molecules, comprising a first part which is competent for cell penetration and a second part which is able to reduce or abolish mast cell degranulation, in particular to reduce or abolish allergy mediators such as histamine secretion from mast cells, wherein the first part is connected to the second part via a linker or a direct bond that creates a conformational constraint by forming a bend or turn.

BACKGROUND OF THE INVENTION

Allergic diseases, including nasal allergy, asthma, urticaria and angioedema, are among the most common diseases encountered by physicians in their clinical practice. Allergy refers to certain diseases in which a wide spectrum of biologically active substances, released from activated mast cells, cause tissue inflammation and organ dysfunction. In essence, any allergic reaction may lead to tissue damage in one or more target organs (see for example Lichtenstein, 1993).

On the cellular level, mast cells are significant mediators of the allergic reaction and are packed with 500 to 1000 granules in which the mediators of the inflammatory reactions are stored. These include vasoactive mediators such as histamine, chemotactic mediators and proteolytic enzymes. In addition, following the activation of mast cells, a number of mediators are generated de novo and released. These include arachidonic acid metabolites such as leukotrienes and prostaglandins and a number of multifunctional cytokines. Mast cell derived factors also recruit and activate additional inflammatory cells, such as eosinophils, neutrophils and mononuclear cells. Therefore, mast cell derived mediators possess all the requisite properties to induce the symptoms of itching, swelling, coughing and choking that are associated with an allergic reaction (Bienenstock et al., 1987). These mediators are released in response to processes which occur through a number of different pathways within mast cells. Thus, therapeutic treatments for allergy and related inflammatory conditions must intervene at some point in the allergenic pathway in order to be effective.

Current therapies against allergy include $H_1$ and $H_2$ blockers, which block the biological activities of histamine. Examples include chlorpheniramine, azatidine, ketotifen, loratidine and others. However, anti-histamines cannot counteract the inflammatory reactions effected by the additional mediators released alongside histamine. Therefore, anti-histamines cannot provide a reliable protection against allergy.

A better allergy treatment would block the secretory process by preventing mast cell degranulation. Drugs which are currently available for this purpose include hydrocortisone and disodium cromoglycate. However, disodium cromoglycate cannot inhibit all types of histamine secretion, and is not always completely effective. Steroids, on the other hand, are effective for blocking mast cell degranulation, but have many unacceptable side effects. Therefore, therapeutic agents which could prevent mast cell degranulation without significant side effects, and could thus prevent or significantly reduce the occurrence of clinical symptoms associated with allergy, such as neurogenic inflammation (see below for details), would be very useful for the treatment of allergy and related conditions.

Mast cell degranulation is a complex process involving at least two different pathways. Mast cells secrete their granular contents in a process of regulated exocytosis (degranulation) by two major pathways, the IgE (immunoglobulin E) dependent pathway and the IgE independent pathway. The IgE dependent pathway is invoked in response to an immunological trigger, brought about by aggregation of the high affinity receptors ($F_{c\in}RI$) for IgE, which are present on the cell surface of mast cells. This response involves crosslinking of cell bound IgE antibodies by the corresponding antigens (allergens).

The IgE-independent or peptidergic pathway is invoked in response to a number of polycationic compounds, collectively known as the basic secretagogues of mast cells. These compounds include the synthetic compound 48/80, naturally occurring polyamines and positively charged peptides, such as the neurotransmitter substance P (Ennis et al., 1980; Sagi-Eisenberg 1993; Chahdi et al., 1998).

The ability of substance P to induce mast cell degranulation, together with the observed presence of mast cells clustered around nerve endings which contain substance P, implicate mast cells as the mediators of substance-P induced neurogenic inflammation (Foreman 1987a,b; Pearce et al., 1989). It is well established that in the skin and elsewhere neurogenic inflammation, through the release of neurotransmitters such as substance P, is a contributor to a variety of diseases such as acute urticaria, psychogenic asthma, interstitial cystitis, bowel diseases, migraines, multiple sclerosis and more (Reviewed by Theoharides 1996). In addition, this IgE independent pathway of degranulation can also be evoked by snake, bee and wasp venoms, bacterial toxins and certain drugs such as opiates.

Although the signal transduction pathways by which mast cell degranulation is activated are not yet fully resolved, a number of cellular events have been shown to occur after stimulation of the mast cells. These include activation of phospholipases such as PLC, PLD and PLA2, elevation of cytosolic $Ca^{2+}$ and activation of serine and tyrosine kinases (reviewed by Sagi-Eisenberg, R. "Signal Transmission Pathways in Mast Cell Exocytosis". In: The Handbook of Immunopharmacology. Academic Press, UK. pp. 71–88, 1993).

Within these processes, however, the involvement of GTP-binding proteins (G-proteins) is well established. For example, the introduction of nonhydrolyzable analogues of GTP, such as GTP-γ-S, into $ATP^{-4}$ permeabilized mast cells, stimulates PLC activity and degranulation.

From these and other observations, the involvement of at least two different G-proteins, one involved in PLC and $Ca^{2+}$ activation ($G_P$) and one directly regulating exocytosis ($G_E$), has been suggested (Gomperts 1990; Gomperts et al., 1991; reviewed by Sagi-Eisenberg 1993). Indeed, it was subsequently demonstrated that basic secretagogues induce histamine secretion by interacting directly with $G_E$, a pertussis toxin-sensitive heterotrimeric G protein, in a receptor-independent manner (Aridor et al., 1990; Aridor & Sagi-Eisenberg 1990). This G-protein was subsequently identified as $Gi_3$, which appears to mediate the peptidergic pathway leading to exocytosis in mast cells. In particular, a synthetic peptide which corresponds to the C terminal sequence of $G\alpha i_3$ (KNNLKECGLY (SEQ ID NO:1)) was able to inhibit histamine release when introduced, into permeabilized mast cells (Aridor et al., 1993).

However, the cell membrane is generally impermeable to most peptides. Therefore, the use of a peptide as a therapeutic agent, directed against an intracellular target, requires a special mechanism to enable the peptide to overcome the membrane permeability barrier.

One possible approach is based on the fusion of the selected peptide with a specific hydrophobic sequence, comprising the "h" region of a signal peptide sequence. Examples of such hydrophobic regions are the signal sequence of the Kaposi fibroblast growth factor (AAVALLPAVLLALLAP (SEQ ID NO:27); Lin et al., 1995; Rojas et al., 1997) and the signal sequence within human integrin $\beta_3$ (VTVLALGALAGVGVG (SEQ ID NO:28); Liu et al., 1996; Review by Hawiger 1997).

Specific importation of biologically active molecules into cells by linking an importation-competent signal peptide to the molecule of interest was disclosed in U.S. Pat. No. 5,807,746, although only in vitro studies were described, such that the signal peptide was not shown to function in vivo. The signal peptide causes the entire complex to be imported into the cell, where theoretically the biologically active molecule could then have its effect. Although such direct importation could serve to introduce the therapeutic compound into the cell, the efficacy of the complex may be limited, such that the biologically active molecule may have little or no effect. The variables which may affect the efficacy of the biologically active molecule include the effect of linking the molecule to the signal peptide, which may result in an inactive hybrid molecule; unpredictable effects of the entire complex within the cell; and even the inability of the entire complex to be imported into the cell, despite the presence of the signal peptide.

In addition, identifying a suitable biologically active molecule for treatment of allergy may also be difficult. For example, linking a non-peptide molecule, such as a known secretion-blocking compound, to a signal peptide is both difficult and may result in an unstable molecule. A peptide could be used as the secretion-blocking compound, but then such a peptide must be carefully selected and tested. Finally, the entire complex would require testing, particularly in vivo, since the ability to penetrate a cell in tissue culture does not necessarily predict the efficacy of the complex in a human or animal subject. U.S. Pat. No. 5,807,746 therefore suffers from the drawback that only in vitro data is disclosed, such that the effect of the signaling peptides in vivo, alone or as part of a complex, is not known. Thus, suitable, targeted, specific therapeutic agents for the treatment of allergy are not currently available and are potentially complex and difficult to develop.

There is therefore a need for, and it would be useful to have, a therapeutic agent for the treatment of allergy and related inflammatory conditions, which would block mast cell degranulation and hence the release of histamine, but which would be specifically targeted to the degranulation pathway and which would therefore have few side effects.

Previous work has demonstrated the ability of several peptides to block mast cell degranulation. For example, a novel peptide designated Peptide 2, that was designed and synthesized to include an importation competent signal peptide, as a first segment at the N-terminus (underlined), and the C-terminal sequence of G$\alpha$i$_3$ as a second segment at the C-terminus (<u>AAVALLPAVLLALLAP</u>KNNLKECGLY, SEQ ID NO:23) inhibited histamine release from activated mast cells (WO 00/78346). Additional active peptides in that disclosure include:

Peptide 2-succ:
    Succinyl-AAVALLPAVLLALLAPKNNLKECGLY;
(SEQ ID NO: 24)

Peptide 5:
    AAVALLPAVLLALLAPKENLKDCGLF; and
(SEQ ID NO: 25)

Peptide 2-cyc:
    AAVALLPAVLLALLAPKNNLKECGLY
(SEQ ID NO: 26)
$$\text{AAVALLPAVLLALLAPKNNLKECGLY} \atop \underline{\hspace{2cm}}\text{-}\varepsilon\text{-NH.}$$

The present invention is not intended to encompass any of the peptides disclosed and claimed in that application, and they are specifically excluded from the present invention, as are any known peptides according to the principles disclosed hereinbelow.

All publications, patents and patent applications mentioned in this specification are herein incorporated in their entirety by reference into the specification, to the same extent as if each individual publication, patent or patent application was specifically indicated to be incorporated herein by reference. In addition, citation of any reference in this application shall not be construed as an admission that such reference is available as prior art to the present invention.

SUMMARY OF THE INVENTION

The present invention discloses a therapeutic complex molecule for the specific, direct and targeted treatment of allergies and related inflammatory conditions, which comprises a first segment which is competent for the importation of the complex molecule into mast cells, and a second segment which is able to block or significantly reduce mast cell degranulation and hence the release of histamine. According to a currently preferred embodiment, the first segment comprises a signal peptide, which is competent for importation of the complex into mast cells, while the second segment comprises a biologically active molecule, such as a peptide, which is able to block the G protein-mediated contribution to the mast cell degranulation process. Most preferred embodiments of the present invention will reduce or abolish inflammatory mediators of allergic reactions, including those late phase inflammatory mediators induced by protein kinase activation, as well as inhibiting histamine secretion from mast cells.

According to the present invention, there is provided an anti-allergic agent, comprising a molecule having at least a first segment competent for importation of the molecule into mast cells, and a second segment for having an anti-allergic effect within the mast cells, the first segment being joined to the second segment through a linker.

According to a preferred embodiment of the present invention, the linker is a covalent bond. According to one currently more preferred embodiment of the present invention the covalent bond is a peptide bond.

It is now disclosed that unexpectedly the linker must be of such a nature as to create a conformational constraint at or near the junction between the first segment and the second segment. Preferably the linker must prevent the first segment from being contiguous to the second segment in a linear or an extended conformation. More preferably it will create a bend or a turn. According to certain currently most preferred embodiments the conformational constraint is selected from the group consisting of, a proline or proline mimetic, an N-alkylated amino acid, a double bond or triple bond or any other moiety which introduces a rigid bend in the peptide backbone.

In addition to Proline, specific examples of moieties which induce suitable conformations include but are not limited to N-methyl amino acids such as sarcosine; hydroxy proline instead of proline; anthranilic acid (2-amino benzoic acid); and 7-azabicyloheptane carboxylic acid.

The second segment has the anti-allergic effect by at least significantly reducing degranulation of the mast cells. Preferably, the second segment is selected from the group consisting of a peptide, a peptidomimetic, and a polypeptide. More preferably, the second segment is a peptide or peptidomimetic. Also more preferably, the first segment is a peptide or peptidomimetic.

It is now disclosed that the second segment comprising the anti-allergic activity most preferably is a peptide having a cyclic conformation. Preferably the cyclic conformation is stabilized by bonds selected from the group consisting of hydrogen bonds, ionic bonds or covalent bonds.

Preferably, the anti-allergic segment of the molecule is a peptide taken from the C terminal sequence of a G protein, more preferably a G protein involved in exocytosis. Specific examples of useful peptides include Gαi$_3$ and Gαt. Most preferably, the anti-allergic segment of the peptide has an amino acid sequence selected from the group of:

a decapeptide derived from Gαi$_3$ having the sequence KNNLKECGLY (SEQ ID NO:1);

a decapeptide derived from Gαt having the sequence KENLKDCGLF (SEQ ID NO:2);

(SEQ ID NO: 3)

KNNLKECGL-para-amino-F (SEQ ID NO:4); KQNLKECGLY (SEQ ID NO:5); KSNLKECGLY(SEQ ID NO:6); KNNLKEVGLY (SEQ ID NO:7) and KENLKECGLY (SEQ ID NO:8).

Within the scope of the present invention are included all active analogues, homologues and derivatives of these sequences, including but not limited to cyclic derivatives.

Preferably the importation competent segment of the molecule is a peptide taken from a signal peptide sequence. Useful examples thereof include the signal peptide sequence of the Kaposi fibroblast growth factor or a human integrin β3.

According to particularly preferred embodiments of the present invention, the molecule is a peptide having an amino acid sequence selected from the group consisting of:

WALL006: AAVALLPAVLLALLAPKQNLKECGLY (SEQ ID NO:11)

WALL007: AAVALLPAVLLALLAPKNNLKEVGLY (SEQ ID NO:12)

WALL008: Succinyl-AAVALLPAVLLALLA-Sar-KNNLKECGLY (SEQ ID NO:13)

WALL010: VTVLALGALAGVGVGPKNNLKECGLY (SEQ ID NO:15)

WALL011: Succinyl-AAVALLPAVLLALLAPKSNLKECGLY (SEQ ID NO:16)

WALL012: Succinyl-AAVALLPAVLLALLAPKENLKECGLY (SEQ ID NO:17)

WALL013: Succinyl-AAVALLPAVLLALLAPKANLKECGLY (SEQ ID NO:18)

WALL014: Succinyl-AAVALLPAVLLALLAP KNNLKECGL-para-amino-F (SEQ ID NO:19)

WALL015: Succinyl-AAVALLPAVLLALLAPKQNLKECGLY(SEQ ID NO:20)

WALL016: Succinyl-AAVALLPAVLLALLAPKNNLKEVGLY (SEQ ID NO:21)

Within the scope of the present invention are included all active analogues, homologues and derivatives of these sequences, including but not limited to cyclic derivatives. In particular, active analogs are intended to include esters, such as but not limited to succinylated derivatives.

According to another embodiment of the present invention, there is provided a pharmaceutical composition for treating an allergic condition in a subject, comprising as an active ingredient a therapeutically effective amount of an anti-allergic agent, said agent comprising a molecule comprising a first segment competent for importation of the molecule into mast cells, and a second segment having an anti-allergic effect within the mast cells, wherein the first part is connected to the second part via a linker or a direct bond that creates a conformational constraint by forming a bend or turn.

According to certain currently most preferred embodiments the conformational constraint is selected from the group consisting of, a praline or proline mimetic, an N alkylated amino acid, a double bond or triple bond or any other moiety which introduces a rigid bend in the peptide backbone.

According to another preferred embodiment of the present invention, the pharmaceutical composition comprises as an active ingredient a complex peptide having as an anti-allergic segment a peptide having an amino acid sequence selected from the group consisting of:

a decapeptide derived from Gαi$_3$ having the sequence KNNLKECGLY (SEQ ID NO:1);

a decapeptide derived from Gαt having the sequence KENLKDCGLF (SEQ ID NO:2);

(SEQ ID NO: 3)

KNNLKECGL-para-amino-Phenylalanine (SEQ ID NO:4); KQNLKECGLY (SEQ ID NO:5); KSNLKECGLY (SEQ ID NO:6); KNNLKEVGLY (SEQ ID NO:7); and KENLKECGLY (SEQ ID NO:8).

Additionally and preferably, the pharmaceutical composition comprises as an active ingredient a complex peptide having an amino acid sequence selected from the group consisting of:

WALL 006: AAVALLPAVLLALLAPKQNLKECGLY (SEQ ID NO:11)

WALL 007: AAVALLPAVLLALLAPKNNLKEVGLY (SEQ ID NO:12)

WALL 008: Succinyl-AAVALLPAVLLALLA-Sar-KNNLKECGLY (SEQ ID NO:13)

WALL 010: VTVLALGALAGVGVGPKNNLKECGLY (SEQ ID NO:15)

WALL 011: Succinyl-AAVALLPAVLLALLAPKSNLKECGLY (SEQ ID NO:16)
WALL012: Succinyl-AAVALLPAVLLALLAPKENLKECGLY (SEQ ID NO:17)
WALL 013: Succinyl-AAVALLPAVLLALLAPKANLKECGLY (SEQ ID NO:18)
WALL 014: Succinyl-AAVALLPAVLLALLAPKNNLKECGL-para-amino-F (SEQ ID NO:19)
WALL 015: Succinyl-AAVALLPAVLLALLAPKQNLKECGLY (SEQ ID NO:20)
WALL016: Succinyl-AAVALLPAVLLALLAPKNNLKEVGLY (SEQ ID NO:21)

Within the scope of the present invention are included all active analogues, homologues and derivatives of these sequences, including but not limited to cyclic derivatives.

According to still another embodiment of the present invention, there is provided a method for treating an allergic condition in a subject, comprising the step of administering a therapeutically effective amount of an anti-allergic agent to the subject, said agent comprising a molecule having at least a first segment competent for importation of the molecule into mast cells, and a second segment for having an anti-allergic effect within the mast cells, wherein the first part is connected to the second part via a linker or a direct bond that creates a conformational constraint by forming a bend or turn.

According to certain currently most preferred embodiments the conformational constraint is selected from the group consisting of, a proline or proline mimetic, an N alkylated amino acid, a double bond or triple bond or any other moiety which introduces a rigid bend in the peptide backbone.

In addition to proline, specific examples of moieties which induce suitable conformations include but are not limited to N-methyl amino acids such as sarcosine; hydroxy proline; anthranilic acid (2-amino benzoic acid); and 7-azabicyloheptane carboxylic acid.

Preferably, the allergic condition is selected from the group consisting of nasal allergy, an allergic reaction in an eye of the subject, an allergic reaction in the skin of the subject, acute urticaria, psoriasis, psychogenic or allergic asthma, interstitial cystitis, bowel diseases, migraines, and multiple sclerosis.

A preferred route of administration is oral, but alternative routes of administration include, but are not limited to, intranasal, intraocular, sub-cutaneous and parenteral administration. More preferably, the therapeutic agent is administered by topical administration. Most preferably, the topical administration is to the skin of the subject. According to an alternative preferred embodiment of the present invention, the therapeutic agent is administered intranasally or by inhalation.

In addition to inhibiting histamine release, it is now disclosed that peptides according to the present invention unexpectedly also inhibit the activation of protein tyrosine kinases (PTKs) and mitogen activated protein kinases (MAPKs). Activation of these protein kinases was demonstrated previously as a crucial event, leading to activation of the late phase inflammatory reactions such as synthesis de novo of leukotrienes and prostaglandins.

According to yet another embodiment of the present invention, there is thus provided a method for preventing late phase inflammatory responses induced by protein kinase activation, comprising the step of administering a therapeutically effective amount of an anti-allergic agent to the subject, said anti-allergic agent comprising a molecule having at least a first segment competent for importation of said molecule into mast cells, and a second segment for having an anti-allergic effect within said mast cells, said first segment being joined to said second segment through a linker, said linker providing a bend or turn at or near the junction between the segments.

According to yet another embodiment of the present invention, there is provided a method for promoting importation of an anti-allergic peptide into a cell of a subject in vivo, the method comprising the steps of:
(a) attaching to the anti-allergic peptide a leader sequence, the leader sequence being a peptide, via a linker or a direct bond which forms a bend or a turn, to form a complex peptide or peptidomimetic molecule;
(b) administering the complex peptide or peptidomimetic molecule to the subject; and
(c) importing the complex molecule into the cell through the leader sequence, such that the anti-allergic peptide is imported into the cell.

Hereinafter, the term "biologically active" refers to molecules, or complexes thereof, which are capable of exerting an effect in a biological system. Hereinafter, the terms "fragment" or "segment" refer to a portion of a molecule or a complex thereof, in which the portion includes substantially less than the entirety of the molecule or the complex thereof.

Hereinafter, the term "amino acid" refers to both natural and synthetic molecules which are capable of forming a peptide bond with another such molecule. Hereinafter, the term "natural amino acid" refers to all naturally occurring amino acids, including both regular and non-regular natural amino acids. Hereinafter, the term "regular natural amino acid" refers to those alpha amino acids which are normally used as components of a protein. Hereinafter, the term "non-regular natural amino acid" refers to naturally occurring amino acids, produced by mammalian or non-mammalian eukaryotes, or by prokaryotes, which are not usually used as a component of a protein by eukaryotes or prokaryotes. Hereinafter, the term "synthetic amino acid" refers to all molecules which are artificially produced and which do not occur naturally in eukaryotes or prokaryotes, but which fulfill the required characteristics of an amino acid as defined above. Hereinafter, the term "peptide" includes both a chain of a sequence of amino acids, whether natural, synthetic or recombinant. Hereinafter, the term "peptidomimetic" includes both peptide analogues and mimetics having substantially similar or identical functionality thereof, including analogues having synthetic and natural amino acids, wherein the peptide bonds may be replaced by other covalent linkages.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
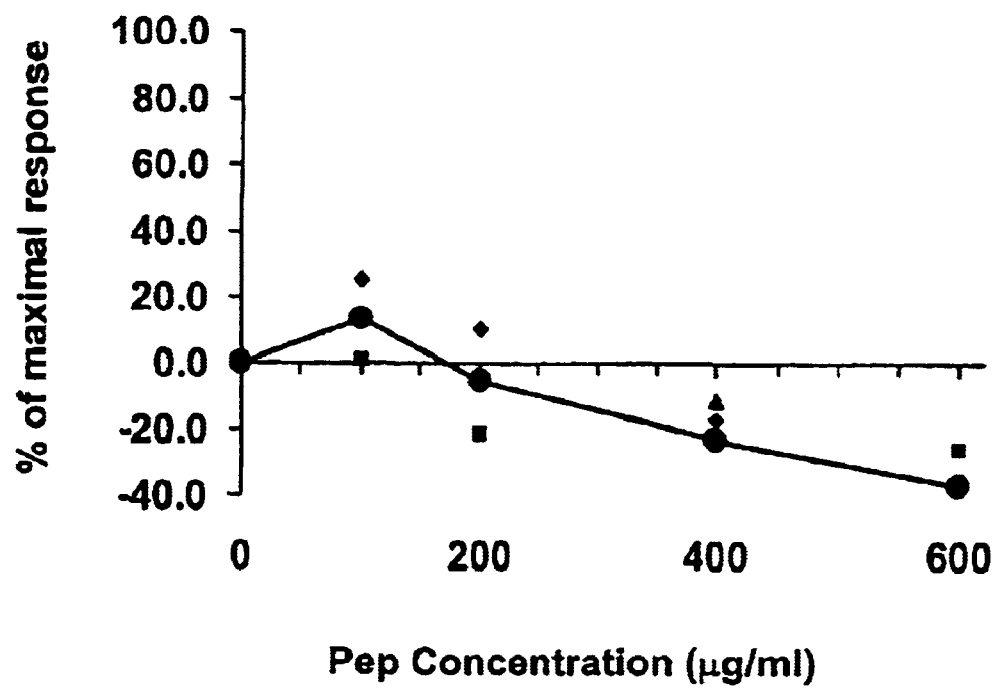
FIG. 1 is a graph of the dose response of peptide WALL006 (1a) on histamine secretion; and (1b) on compound 48/80 induced histamine release from intact mast cells.

The present invention discloses a therapeutic complex molecule for the specific, direct and targeted treatment of allergies and related inflammatory conditions, which comprises molecules having at least a first segment which is competent for the importation of the complex into mast cells, and a second segment which is able to block or significantly reduce mast cell degranulation and hence the release of histamine.

It is now disclosed that the linker is a crucial element of the present invention, and that it must impose certain conformational constraints at or near the junction of the two segments of the molecule. The first segment is connected to the second segment through a linker or a direct bond, the linker creating a conformational constraint, by forming a bend or turn. According to certain currently most preferred embodiments the conformational constraint is selected from the group consisting of, a proline or proline mimetic, an N alkylated amino acid, a double bond or triple bond or any other moiety which introduces a rigid bend into the peptide backbone.

In addition to proline, specific examples of moieties which induce suitable conformations include but are not limited to N-methyl amino acids such as sarcosine, hydroxy proline, anthranilic acid (2-amino benzoic acid) and 7-azabicycloheptane carboxylic acid.

The first segment is a molecule, preferably a peptide or a peptidomimetic, and more preferably a signal peptide. A signal peptide is a peptide which is capable of penetrating through the cell membrane, to permit the exportation and/or importation of proteins or peptides. As used herein, suitable signal peptides are those which are competent for the importation of proteins, peptides or other molecules into the cell. Such signal peptides generally feature approximately 10–50 amino acids, of which the majority are typically hydrophobic, such that these peptides have a hydrophobic, lipid-soluble portion. Preferably, signal peptides are also selected according to the type of cell into which the complex is to be imported, such that signal peptides produced by a particular cell type, or which are derived from peptides and/or proteins produced by that cell type, can be used to import the complex into cells of that type. Examples of such signal peptides are described above and are also disclosed in U.S. Pat. No. 5,807,746, incorporated by reference as if fully set forth herein for the teachings regarding signal peptides.

The second segment is a molecule which has an anti-allergic effect, preferably by preventing mast cell degranulation, and hence the release of histamine from these mast cells. The molecule is preferably a peptide, and more preferably a peptide derived from the C terminal sequence of $G\alpha i_3$, which appears to mediate the peptidergic pathway leading to exocytosis in mast cells. Alternatively, the second segment is selected from the group consisting of a peptidomimetic, a polypeptide, or a protein.

The linker which connects the first segment to the second segment is preferably a covalent bond. Conveniently, the covalent bond may be a peptide bond if at least one of the first and second segments is a peptide. It is now disclosed that the linker is a crucial element of the present invention, and that it must impose certain conformational constraints at or near the junction of the two segments of the molecule.

The first part is connected to the second part via a linker or a direct bond that creates a conformational constraint by forming a bend or turn. According to certain currently most preferred embodiments the conformational constraint is selected from the group consisting of, a proline or proline mimetic, an N alkylated amino acid, a double bond or triple bond or any other moiety which introduces a rigid bend in the peptide backbone.

In addition to proline, specific examples of moieties which induce suitable conformations include but are not limited to N-methyl amino acids such as sarcosine, hydroxy proline, anthranilic acid (2-amino benzoic acid) and 7-azabicycloheptane carboxylic acid.

A range of methods of creating suitably constrained conformations at or near the junction of the complex molecules of the invention are well known in the art. Classical methods of introducing conformational constraints include structural alteration of amino acids or introduction of bonds other than a flexible peptide bond. In addition to other modes of conformational restriction, such as configurational and structural alteration of amino acids, local backbone modifications, short-range cyclization, medium and long range cyclizations [Hruby, V. J., Life Sci. 31, 189 (1982); Kessler, H., Angew. Chem. Int. Ed. Eng.,21, 512 (1982); Schiller, P. W., in The Peptides, Udenfriend, S., and Meienhofer, J. Eds., Volume 6 p. 254 (1984); Veber, D. F. and Freidinger, R. M., Trends in Neurosci. 8, 392 (1985); Milner-White, E. J., Trends in Pharm. Sci. 10, 70 (1989)] are useful to optimize the active conformations of the peptides according to the invention.

Therapeutically active peptides are cyclized to achieve metabolic stability, to increase potency, to confer or improve selectivity and to control bioavailability. The possibility of controlling these important pharmacological characteristics through cyclization of linear peptides prompted the use of medium and long range cyclization to convert natural bioactive peptides into peptidomimetic drugs, as is known in the art. Cyclization also brings about structural constraints that enhance conformational homogeneity and facilitates conformational analysis [Kessler, H., Angew. Chem. Int. Ed. Eng., 21, 512 (1982)]. Moreover, the combination of structural rigidification-activity relationship studies and conformational analysis gives insight into the biologically active conformation of linear peptides.

The present invention also discloses methods for treating allergies. Hereinafter, the term "treatment" includes both the prevention of the allergic condition, as well as the substantial reduction or elimination of allergic symptoms. Allergic conditions for which the therapeutic agents of the present invention are useful include, but are not limited to, nasal allergy, irritation or allergic reactions in the eyes, allergic reactions in the skin including any type of allergen-induced rash or other skin irritation or inflammation, acute urticaria, psoriasis, psychogenic or allergic asthma, interstitial cystitis, bowel diseases, migraines, and multiple sclerosis.

Such treatment may be performed topically, for example for skin allergies and allergic reactions, including but not limited to, contact dermatitis in reaction to skin contact with an allergen; reactions to insect bites and stings; and skin reactions to systemic allergens, such as hives appearing after a food substance has been ingested by the subject. Alternatively and/or additionally, such treatment may be performed by systemic administration of the therapeutic complex. A preferred route of administration is oral, but alternative routes of administration include, but are not limited to, intranasal, intraocular, sub-cutaneous and parenteral administration. Other routes of administration, and suitable pharmaceutical formulations thereof, are described in greater detail below.

As noted previously, in a certain currently most preferred embodiment of the present invention, the first and the second segments are both peptides, which are joined with a peptide bond.

In the present invention, novel peptides were tested, designated as peptides:

WALL004: AAVALLPAVLLALLAAKNNLKECGLY (SEQ ID NO:9)
WALL005: AAVALLPAVLLALLAPKNNLKECGL-para-amino-F (SEQ ID NO:10)
WALL006: AAVALLPAVLLALLAPKQNLKECGLY (SEQ ID NO:11)
WALL007: AAVALLPAVLLALLAPKNNLKEVGLY (SEQ ID NO:12)
WALL008: Succinyl-AAVALLPAVLLALLA-Sar-KNNLKECGLY (SEQ ID NO:13)
WALL010: VTVLALGALAGVGVGPKNNLKECGLY (SEQ ID NO:15)
WALL011: Succinyl-AAVALLPAVLLALLAPKSNLKECGLY (SEQ ID NO:16)
WALL012: Succinyl-AAVALLPAVLLALLAPKENLKECGLY (SEQ ID NO:17)
WALL013: Succinyl-AAVALLPAVLLALLAPKANLKECGLY (SEQ ID NO:18)
WALL014: Succinyl-AAVALLPAVLLALLAPKNNLKECGL-para-amino-F (SEQ ID NO:19)
WALL015: Succinyl-AAVALLPAVLLALLAPKQNLKECGLY (SEQ ID NO:20)
WALL016: Succinyl-AAVALLPAVLLALLAPKNNLKEVGLY (SEQ ID NO:21)
WALL023: AAVALLPAVLLALLAPYLGCEKLNNK (SEQ ID NO:22)

Previously (WO 00/78346) it has been shown that certain peptides designed and synthesized to include distinct importation competent signal peptides as a first segment at the N-terminus and the C-terminal sequences of Gαi$_3$ or Gαt at the C-terminus as a second segment were active and are listed as follows:

Peptide 2: AAVALLPAVLLALLAPKNNLKECGLY (SEQ ID NO:23)
Peptide 2-succ: Succinyl-AAVALLPAVLLALLAPKNNLKECGLY (SEQ ID NO:24)
Pep 5: AAVALLPAVLLALLAPKENLKDCGLF (SEQ ID NO:25)

(SEQ ID NO: 26)
Peptide 2-Cyc:

In addition, the following peptide was previously synthesized and shown to be inactive: VTVLAL-GALAGVGVGKNNLKECGLY (SEQ ID NO:14).

This peptide was previously designated as Peptide 1 and is designated herein below as WALL009 for the sake of comparison to the novel peptides of the invention.

These known peptides disclosed and claimed previously are explicitly excluded from the present invention.

The novel peptides were examined in-vitro for their ability to block compound 48/80 induced histamine secretion from purified rat peritoneal mast cells. Peptides which are active in this screening could therefore be useful for mast cell dependent allergies. Such allergies include but are not limited to those in which mast cell degranulation is mediated through the IgE-independent pathway from which the second segment of the above peptides was taken. Examples of such allergies include but are not limited to neurogenic inflammation in the skin and elsewhere, including but not limited to, acute urticaria, psoriases, psychogenic asthma, interstitial cystitis, bowel diseases, migraines, and multiple sclerosis.

The principles of the present invention are illustrated herein with the following examples, which are to be construed in a non-limitative manner. The skilled artisan will appreciate that many modifications and variations of the specific embodiments exemplified are possible within the scope of the present invention.

EXAMPLE 1

Testing of Peptides in vitro

Peptides of the present invention, as described above, were tested in vitro for their ability to block histamine secretion from mast cells. Rat peritoneal mast cells were chosen as the experimental model, since it was previously shown that both rat peritoneal and human skin mast cells release histamine in response to substance P by an IgE-independent mechanism (Devillier et al., 1986; Foreman 1987a,b; Columbo et al., 1996). It was also demonstrated that the same peptidergic pathway is involved in both rat peritoneal and human cutaneous mast cells (Mousli et al., 1994; Emadi-Khiav et al., 1995).

Compound 48/80 was chosen as the allergen since it is one of the polycationic compounds, collectively known as the basic secretagogues of mast cells. Compound 48/80 has been shown to induce degranulation of human mast cells. In particular, it is very active on skin mast cells. Compound 48/80 has been used as a diagnostic agent in vivo to assess the release ability of human mast cells, to determine the effectiveness of drugs against chronic urticaria and to study itch and flare responses in atopic dermatitis (Kivity et al., 1988; Goldberg et al., 1991). Therefore inhibition of compound 48/80 induced histamine release is applicable and relevant to prevention of allergy induced by other basic secretagogues such as substance P, snake, bee and wasp venoms, bacterial toxins and certain drugs such as opiates.

The ability of each of the tested peptides to inhibit mast cell degranulation, when induced compound 48/80, was then tested. The experimental methods were as follows.

Materials and Methods

Peptide Synthesis

Peptides were synthesized by PolyPeptide laboratories (Wolfenbuttel, Germany). Peptides were synthesized by the solid phase methodology and supplied at >95% purity. The correct composition and purity of the peptide were verified by HPLC, mass spectrometry and amino acid analysis. Lyophilized peptides were kept at −20° C. Peptides stock solutions (5 mg/ml in 10% dimethylsulfoxide (DMSO) in $H_2O$) were freshly prepared for each experiment.

Isolation and Purification of Mast Cells

Mast cells from the peritoneal cavity of C.R rats were isolated in Tyrode buffer (137 mM NaCl, 2.7 mM KCl, 1 mM $MgCl_2$, 0.4 mM $NaH_2PO_4$, 20 mM Hepes, 1.0 mM $CaCl_2$, 5.6 mM glucose, 1 mg/ml BSA, pH 7.2) and purified over a Ficoll gradient. A suspension of washed peritoneal cells was placed over a cushion of 30% Ficoll 400 (Pharmacia Biotech.) in buffered saline containing 0.1% BSA, and centrifuged at 150×g for 15 min. The purity of mast cells recovered from the bottom of the tube was >90%, as assessed by toluidine blue staining.

Triggering Histamine Secretion from Intact Cells

Purified mast cells ($10^5$ cells/0.5 ml in duplicates) were incubated in Tyrode buffer with buffer or with desired concentrations of the indicated peptide for 2 h at 37° C. Histamine secretion was subsequently stimulated by 0.1 μg/ml of compound 48/80 (Sigma) dissolved in Tyrode buffer. Incubation with compound 48/80 was carried out for 20 min at 37° C. The reaction was terminated by placing the tubes on ice. The cells were sedimented by centrifugation at a brief spin (12,000 g×20 s) and the supernatants were collected. The amount of histamine release was determined as previously described (Aridor et al., 1990). Briefly, cell pellets were lysed using 0.1 ml of 0.1N NaOH and the volume of each sample was adjusted to 0.5 ml by $H_2O$. Histamine content was assayed using the O-phthalaldehyde (OPT) fluorimetric method (Shore et al., 1959). Aliquots of 0.4 ml from the supernatants and cell lysates were incubated with 1.6 ml $H_2O$, 0.4 ml 1N NaOH and 0.1 ml of 10 mg/ml OPT in methanol, for 4 min. at room temperature. The reaction was terminated by the addition of 0.2 ml 3N HCl. Samples were centrifuged at 150×g for 5 min. and 0.2 ml samples were transferred to a 96 well plate. The histamine spectrofluorimetric assay was run in microplates using a microplate reader (FL-600, Biotek Instruments Winooski, Vt., USA). Samples were excited by light at 340 nm and read at 440 nm. Histamine release was calculated as the percentage of total histamine content (supernatant/pellet+supernatant) in each sample. Each data point represents the average of duplicate measurements. The spontaneously released histamine was subtracted. Statistical analysis and plotting were done with Excel® (Microsoft Ltd., Washington, USA).

Activation of PTK (Protein Tyrosine Kinase) and MAP Kinase

Purified mast cells ($10^5$ cells/0.5 ml) were incubated in Tyrode's buffer in the presence of 0.1 mM vanadate in the absence or presence of 600 μg/ml of peptide 2 for 1 h at 37° C. The cells were triggered by 5 μg/ml of compound 48/80 (Sigma) dissolved in Tyrode's buffer or by $H_2O_2/VO_3$ for 20-min incubation period at 37° C. At the end of incubation, the cells were sedimented and cells extracts were prepared. The samples were resolved by SDS/10% PAGE and immunoblotted with anti-phospho-Tyr and anti active MAPK antibodies.

EXAMPLE 2

Peptide Modifications

Results disclosed previously (International Patent Application serial no. WO 00/78346) have demonstrated the ability of several peptides to block mast cell degranulation. For example, a novel peptide, that was designed and synthesized to include an importation competent signal peptide, as a first segment at the N-terminus (underlined), and the C-terminal sequence of Gαi3 as a second segment at the C-terminus (AAVALLPAVLLALLAPKNNLKECGLY (SEQ ID NO:29)) inhibited histamine release from activated mast cells.

The present invention is based on results of structure activity relationship studies using several novel peptides, in which point mutations or chemical modifications were introduced. These novel peptides were designed and tested to achieve the following aims:

Aim I: To improve biological efficacy.

Aim II: To increase peptide stability and/or solubility.

Aim III: To define amino acid residues which are essential for activity and therefore cannot be replaced without loss of activity.

Aim IV: To determine the structure/function relationships.

To address these aims, we have synthesized novel peptides as demonstrated below.

1. Peptide WALL006 Computer modeling of the active molecule have demonstrated that the Asparagine at position 18 of the peptide, which is position 2 of the active anti-allergic sequence, is important in order to preserve the cyclic 3-D structure of the active anti-allergic moiety within the peptide. According to the computerized model, a hydrogen bond links this Asparagine with the Tyrosine residue at position 26 (International Patent application WO 00/78346). To test this hypothesis, the Asparagine residue at position 18, was replaced by Glutamine to form peptide WALL006.

Peptide WALL006: AAVALLPAVLLALLAPKQN-LKECGLY (SEQ ID NO:11)

In this example we have shown that replacement of the Asn with Glutamine (peptide WALL006) resulted in an active, though less potent peptide.

Further substitutions included replacing this Asparagine with Serine, Alanine, or Glutamic acid as well as replacing the tyrosine at position 28 with Para-Amino-Phenyl alanine. All the mutated peptides were also synthesized with a succinyl group linked to their N-terminus in order to increase their solubility. The purpose of these substitutions was to evaluate the contribution of the putative hydrogen bond between the amino acid at position 18 and the Tyrosine residue and to compare the activities of peptides carrying at position 18 either a neutral, or polar or charged amino acid.

2. Peptide WALL015 This sequence is identical to WALL006 but includes a Succinyl group at the N-terminus.

Peptide WALL 015: Succinyl-AAVALLPAVLLALLAPKQNLKECGLY (SEQ ID NO:20)

3. Peptide WALL 011 The Asparagine residue at position 18, was replaced by Serine to form peptide WALL011.

Peptide WALL 011: Succinyl-AAVALLPAVLLALLAPKSNLKECGLY (SEQ ID NO:16)

4. Peptide WALL 012 The Asparagine residue at position 18, was replaced by Glutamic Acid to form peptide WALL012.

Peptide WALL 012: Succinyl-AAVALLPAVLLALLAPKENLKECGLY (SEQ ID NO:17)

5. Peptide WALL 013 The Asparagine residue at position 18, was replaced by Alanine to form peptide WALL013.

Peptide WALL 013: Succinyl-AAVALLPAVLLALLAPKANLKECGLY (SEQ ID NO: 18)

6. Peptide WALL005 The Tyrosine residue at the C-terminal end of the peptide, at position 26, was replaced by para-amino-phenylalanine, which can also form a hydrogen bond, in a similar fashion to the OH group in Tyrosine, to form peptide WALL005.

Peptide WALL005: AAVALLPAVLLALLAPKNNLKECGL-para-amino-F (SEQ ID NO:10)

7. Peptide WALL 014 A succinylated form of peptide WALL005.

Peptide WALL 014: Succinyl-AAVALLPAVLLALLAPKNNLKECGL-para-amino-F (SEQ ID NO: 19)

8. Peptide WALL007-In an attempt to improve peptide efficacy and also to avoid possible oxidation of the peptide, and thereby to increase its stability, the cysteine residue at position 23 was replaced by valine, to form peptide WALL007.

Peptide WALL007: AAVALLPAVLLALLAP-KNNLKEVGLY (SEQ ID NO:12)

9. Peptide WALL016-to the succinylated form of WALL007.

Peptide WALL016: Succinyl-AAVALLPAVLLALLAPKNNLKEVGLY (SEQ ID NO:21)

In order to assess the importance of the linkage between the two parts of the complex peptide and especially the importance for biological activity of the proline residue as the point of junction between the importation segment and the functional moiety, the following peptides were synthesized and tested.

10. Peptide WALL004-The proline at position 16, at the point of junction between the importation segment and the functional moiety, was replaced by Alanine, to form peptide WALL004.

Peptide WALL004: AAVALLPAVLLAL-LAAKNNLKECGLY (SEQ ID NO:9)

To establish the importance of the rigid turn or bend as provided by the Proline three additional peptides were synthesized and tested for biological activity:

11. Peptide WALL008 In which Sarcosine replaces the Proline. The addition of Succinyl again is to increase solubility.

Peptide WALL008: Succinyl-AAVALLPAVLLALLA-Sar-KNNLKECGLY (SEQ ID NO:13)

12. Peptide WALL009 This is a sequence that was shown previously to be inactive (disclosed in WO 00/78346), but contains the same active anti-allergic sequence (last 10 amino acids) and has no solubility problems.

Peptide WALL009: VTVLAL-GALAGVGVGKNNLKECGLY (SEQ ID NO:14)

13. Peptide WALL010 This is the same inactive sequence as in WALL009, but this novel peptide includes a Proline residue that is now connecting the leader sequence to the active sequence. This peptide was synthesized to test whether inclusion of a rigid amino acid (proline) that forms a bend at the junction of the two segments may convert it into an active peptide.

Peptide WALL010: VTVLALGALAGVGVGP-KNNLKECGLY (SEQ ID NO:15)

14. Peptide WALL023: In order to create a peptide that could serve as negative control to the active sequence of G$\alpha$i$_3$, the last 10 amino acids of peptide 2 were replaced by an anti-sense sequence.

Peptide WALL023: AAVALLPAVLLALLAPYLGCEK-LNNK (SEQ ID NO:22)

Experimental Results

1) Peptide WALL006: AAVALLPAVLLALLAPKQN-LKECGLY (SEQ ID NO:11)

Incubation of purified intact mast cells in vitro with increasing concentrations of Peptide WALL006 did not result in histamine secretion. In fact, incubation with the peptide resulted in inhibition of the basal level of histamine secretion, when compared to control cells (illustrated in FIG. 1A). These results have indicated that Peptide WALL006 is unlikely to cause allergic side effects. Next, this peptide was tested for its ability to block compound 48/80 induced histamine secretion. For this purpose, mast cells were incubated with increasing concentrations of the peptide, prior to their trigger with compound 48/80.

Figure 1B:
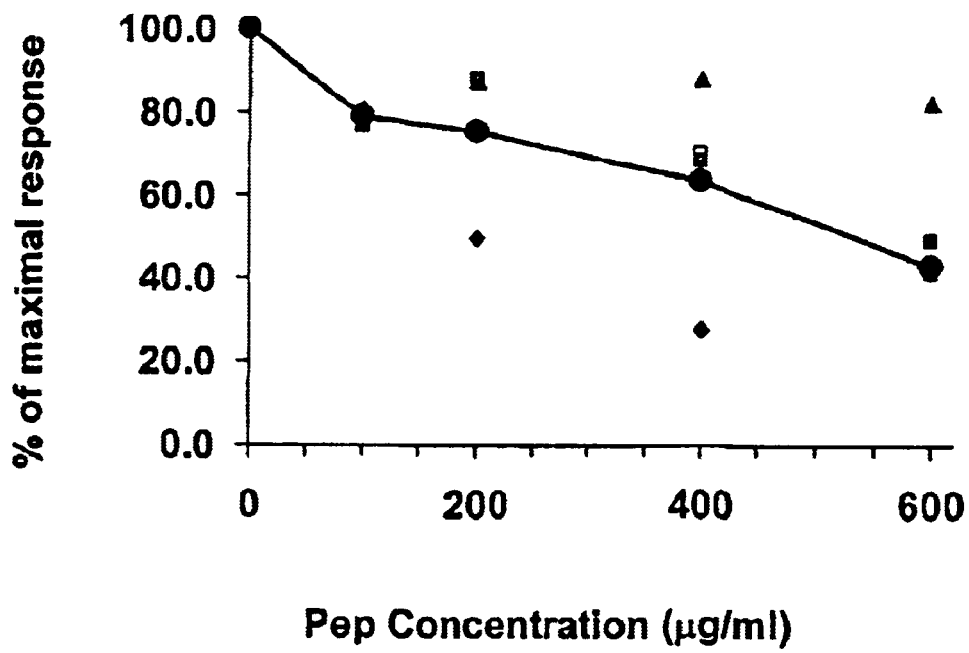

As shown in FIG. 1B, peptide WALL006 blocked compound 48/80 induced histamine secretion in a dose dependent manner, with IC$_{50}$ value of 560 µg/ml and maximal inhibition of 57% at concentration of 600 µg/ml.

These results demonstrate that substitution of the Asparagine residue at position 18 with Glutamine, resulted in an active peptide, which inhibits histamine secretion from isolated mast cells. However Peptide WALL006, while still active, is less potent than the original, unmodified peptide (Peptide 2 in Patent application WO 00/78346).

2) Peptide WALL015: Succinyl-AAVALLPAVLLALLAPKQNLKECGLY (SEQ ID NO:20)

Figure 2A:
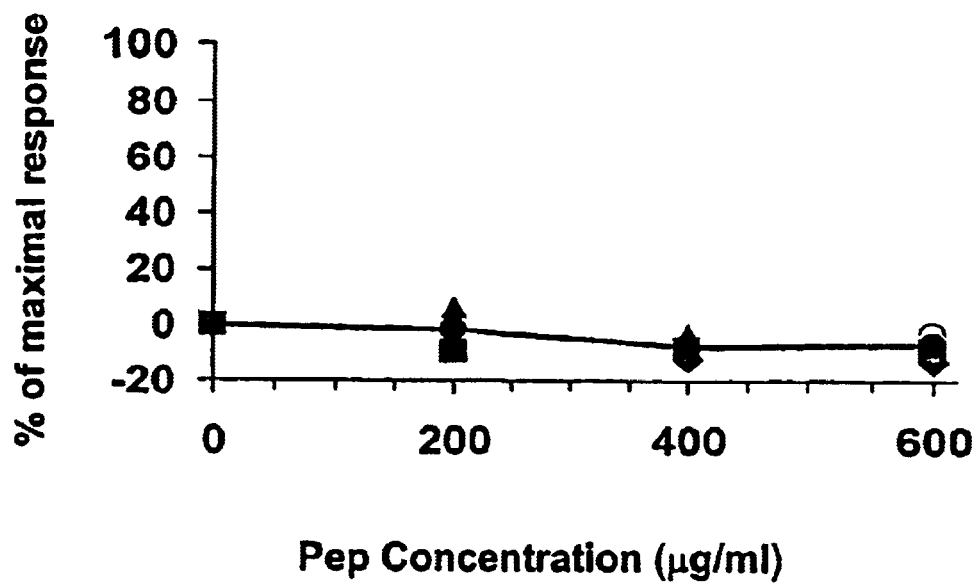
FIG. 2 is a graph of the dose response of peptide WALL015 (2a) on histamine secretion; and (2b) on compound 48/80 induced histamine release from intact mast cells.
Figure 2B:
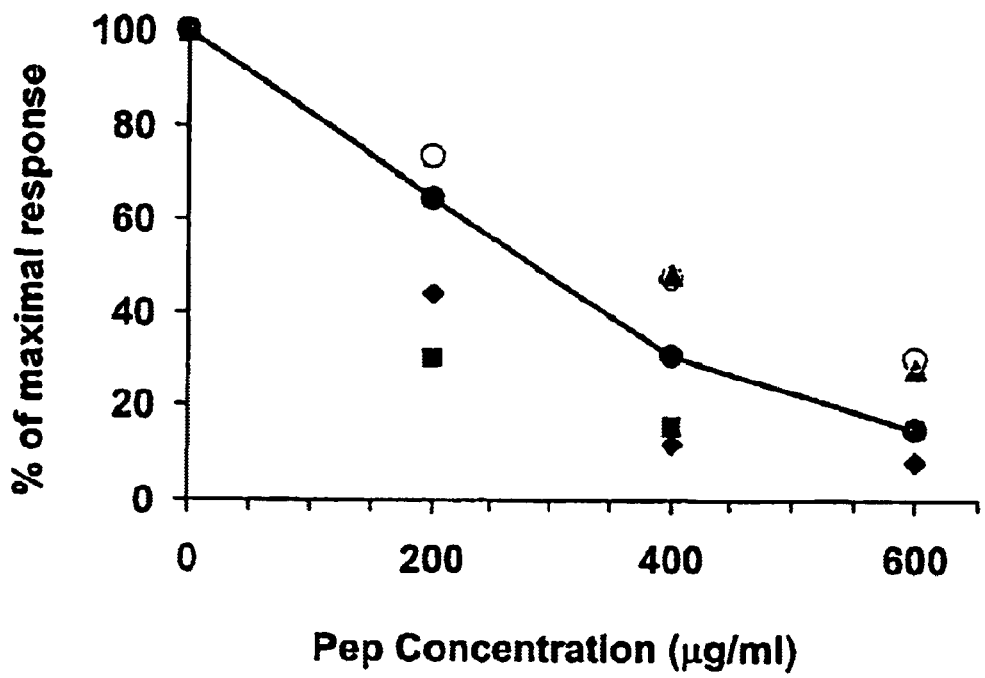

Incubation of purified intact mast cells in vitro with increasing concentrations of peptide WALL015 did not result in histamine secretion (FIG. 2A). In fact, incubation with the peptide resulted in minor inhibition of the basal level of histamine secretion, when compared to control cells (illustrated in FIG. 2A). These results have indicated that peptide WALL015 is unlikely to cause allergic side effects. Next, this peptide was tested for its ability to inhibit the histamine secretion induced by compound 48/80. For this purpose, mast cells were incubated with increasing concentrations of the peptide, prior to their trigger with compound 48/80. As shown in FIG. 2B, peptide WALL015 blocked compound 48/80 induced histamine secretion in a dose dependent manner, with $IC_{50}$ values of 300 µg/ml and maximal inhibition of 75% at concentration of 600 µg/ml.

These results demonstrated that a peptide sequence identical to WALL006 that includes an addition of a Succinyl at the N-terminus, can serve as a more efficient blocker of histamine secretion from mast cells, as compared to the non-succinylated form.

3) Peptide WALL011: Succinyl-AAVALLPAVLLALLAPKSNLKECGLY (SEQ ID NO:16)

Figure 3A:
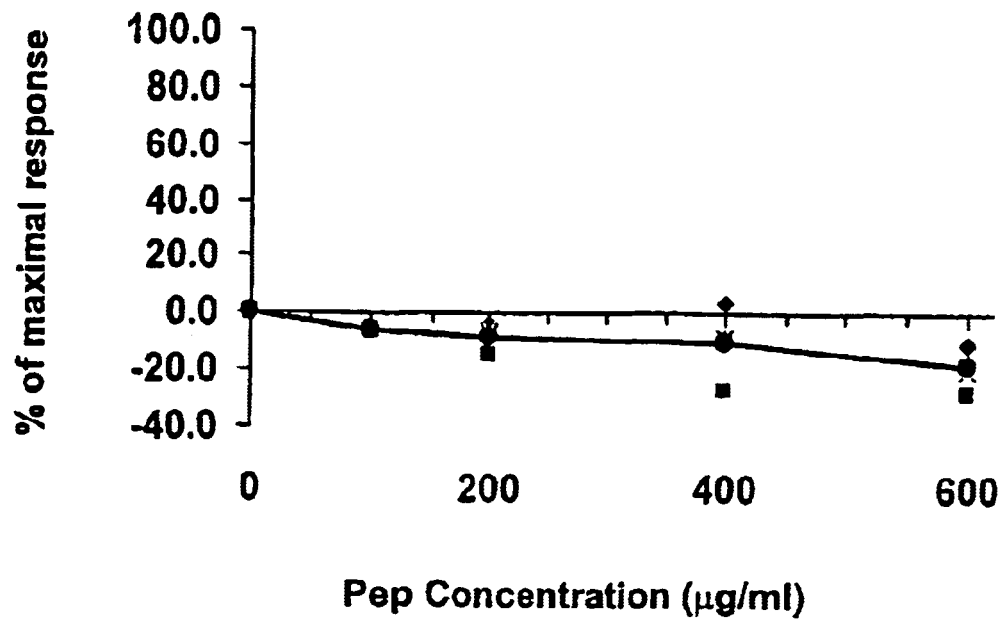
FIG. 3 is a graph of the dose response of peptide WALL011 (3a) on histamine secretion; and (3b) on compound 48/80 induced histamine release from intact mast cells.
Figure 3B:
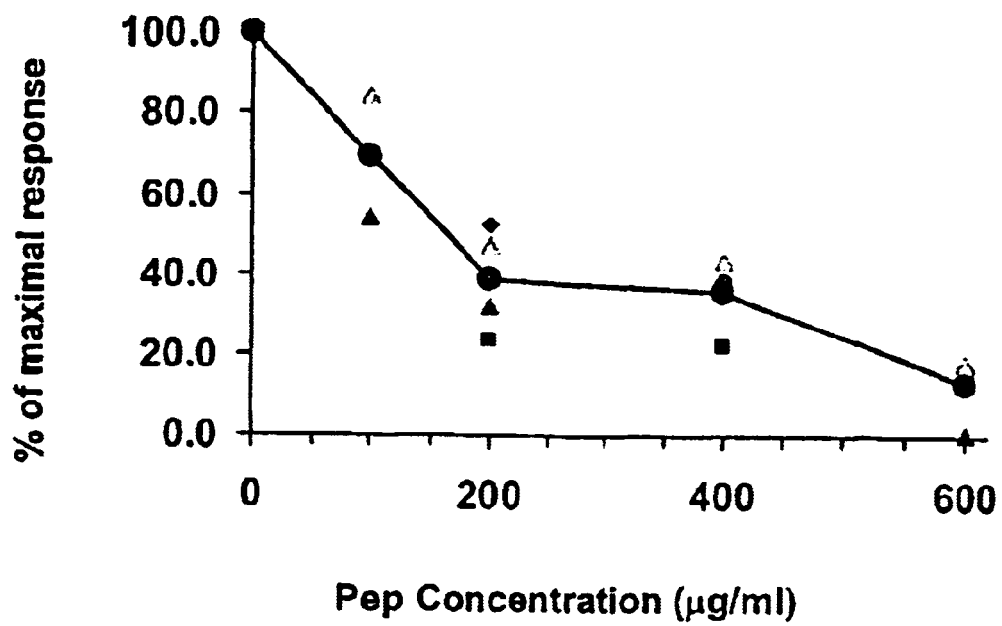

Incubation of purified intact mast cells in vitro with increasing concentrations of peptide WALL011 did not result in histamine secretion (FIG. 3A). Moreover, incubation with the peptide at concentration of 400–600 µg/ml resulted in a minor inhibition of the basal level of histamine secretion, when compared to control cells (illustrated in FIG. 3A). These results have indicated that peptide WALL011 is unlikely to cause allergic side effects. Next, this peptide was tested for its ability to inhibit the histamine secretion induced by compound 48/80. For this purpose, mast cells were incubated with increasing concentrations of the peptide, prior to their trigger with compound 48/80. As shown in FIG. 3B, peptide WALL011 inhibited compound 48/80 induced histamine secretion in a dose dependent manner, with $IC_{50}$ values of 160 µg/ml and maximal inhibition of 87% at concentration of 600 µg/ml.

These results demonstrate that substitution of Asparagine residue at position 18 in the peptide sequence with Serine, resulted in an active peptide, which inhibits histamine secretion from isolated mast cells.

4) Peptide WALL012: Succinyl-AAVALLPAVLLALLAPKENLKECGLY (SEQ ID NO: 17)

Figure 4A:
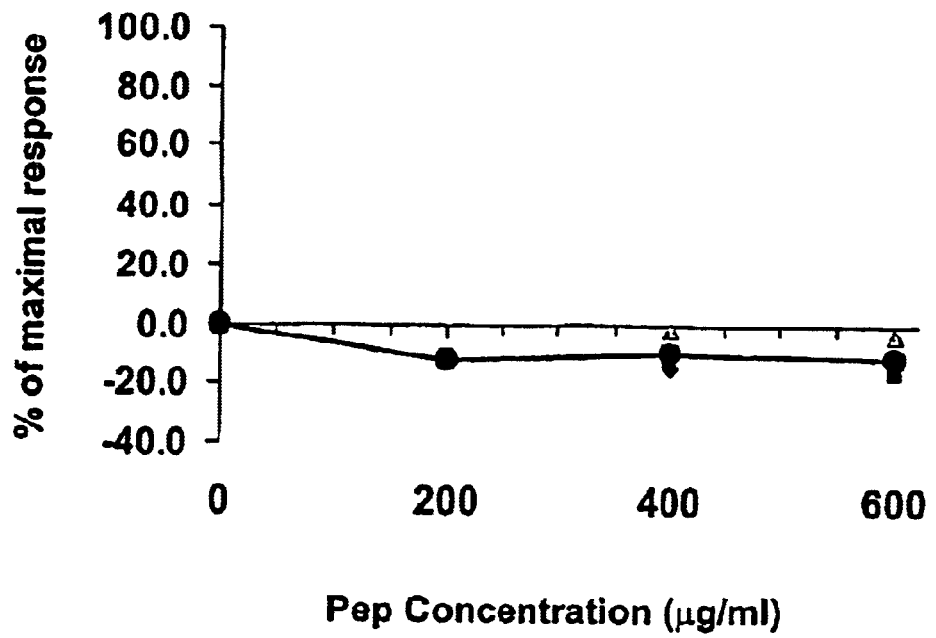
FIG. 4 is a graph of the dose response of peptide WALL012 (4a) on histamine secretion; and (4b) on compound 48/80 induced histamine release from intact mast cells.
Figure 4B:
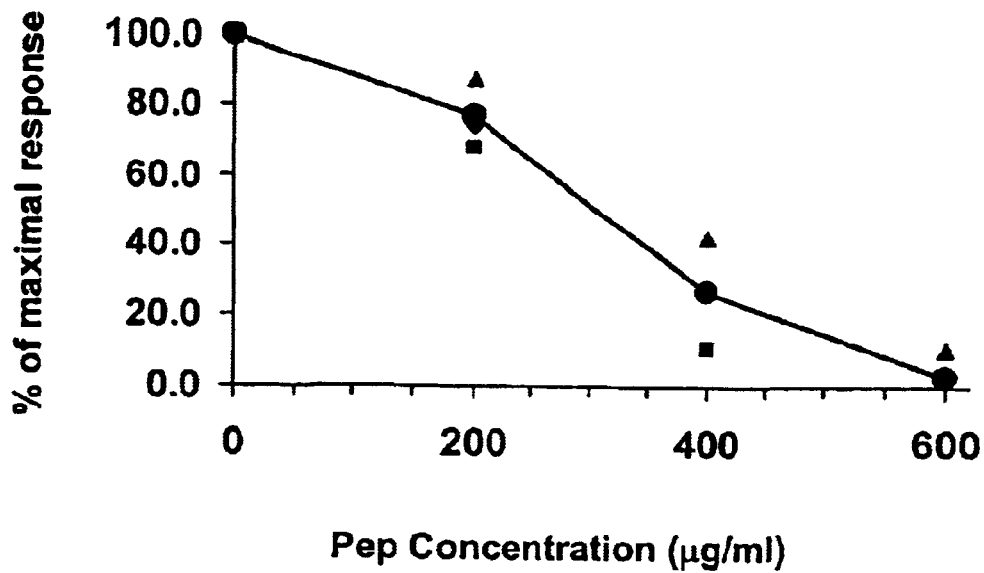

Incubation of purified intact mast cells in vitro with increasing concentrations of peptide WALL012 did not result in histamine secretion (FIG. 4A). Furthermore, incubation with the peptide resulted in a minor inhibition of the basal level of histamine secretion, when compared to control cells (illustrated in FIG. 4A). These results have indicated that peptide WALL012 is unlikely to cause allergic side effects. Next, this peptide was tested for its ability to inhibit the histamine secretion induced by compound 48/80. For this purpose, mast cells were incubated with increasing concentrations of the peptide, prior to their trigger with compound 48/80. As shown in FIG. 4B, peptide WALL012 blocked compound 48/80 induced histamine secretion in a dose dependent manner, with $IC_{50}$ values of 320 µg/ml and maximal inhibition of 97.5% at concentration of 600 µg/ml.

These results demonstrate that substitution of Asparagine residue at position 18 with Glutamic acid, resulted in an active peptide, which inhibits histamine secretion from isolated mast cells.

5) Peptide WALL013: Succinyl-AAVALLPAVLLALLAPKANLKECGLY (SEQ ID NO: 18)

Figure 5A:
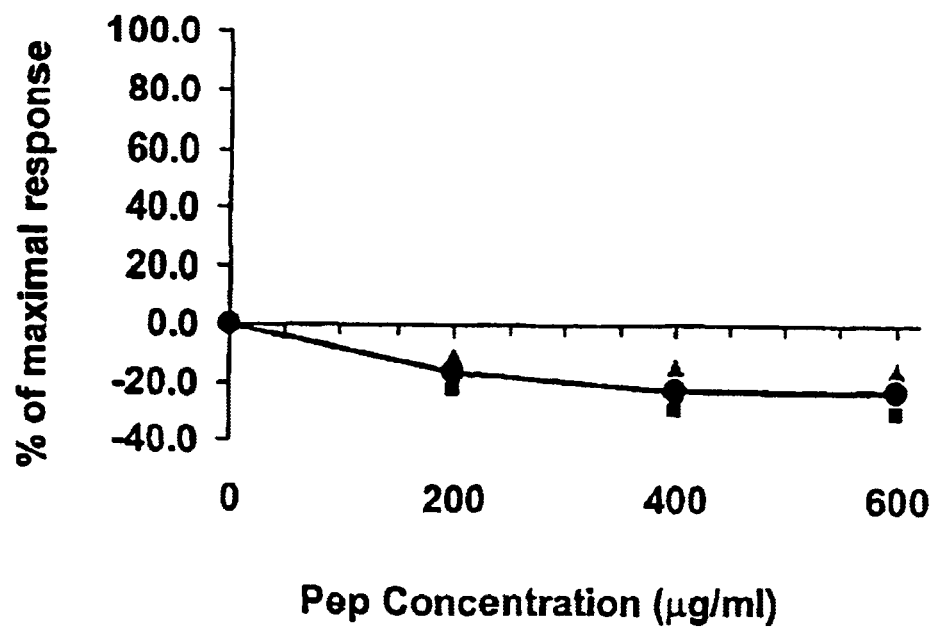
FIG. 5 is a graph of the dose response of peptide WALL013 (5a) on histamine secretion; and (5b) on compound 48/80 induced histamine release from intact mast cells.
Figure 5B:
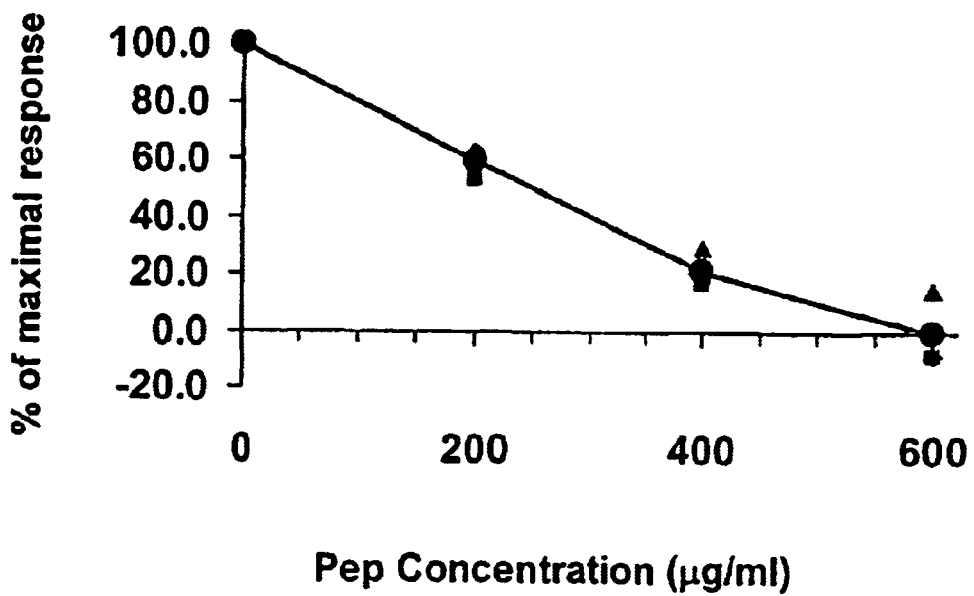

Incubation of purified intact mast cells in vitro with increasing concentrations of peptide WALL013 did not result in histamine secretion (FIG. 5A). In fact, incubation with the peptide resulted in a minor inhibition of the basal level of histamine secretion, when compared to control cells (illustrated in FIG. 5A). These results have indicated that peptide WALL013 is unlikely to cause allergic side effects. Next, this peptide was tested for its ability to inhibit histamine secretion induced by compound 48/80. For this purpose, mast cells were incubated with increasing concentrations of the peptide, prior to their trigger with compound 48/80. As shown in FIG. 5B, peptide WALL013 blocked compound 48/80 induced histamine secretion in a dose dependent manner, with IC50 values of 245 µg/ml and maximal inhibition of 100% at concentration of 600 µg/ml.

Results obtained with peptides WALL006, WALL011, WALL012 WALL013 and WALL015 demonstrate that replacement of the Asparagine at position 18 with one of the following: Glutamine, Serine, Glutamic acid or Alanine result in active peptides that significantly inhibit histamine secretion from mast cells. Since Asparagine, Glutamine, Serine, and Glutamic acid are capable of forming a hydrogen bond with the tyrosine residue located at the C-terminal end of the peptide, it is suggested that the formation of a cyclic three-dimensional structure might be mediated by this bond. However since Alanine is not capable of forming a hydrogen bond and yet results in an active peptide we assume that other connections are also involved and contribute to the formation of the active cyclic three-dimensional structure.

6) Peptide WALL005: AAVALLPAVLLALLAP NNLKECGL-para-amino-F (SEQ ID NO:10)

Figure 6A:
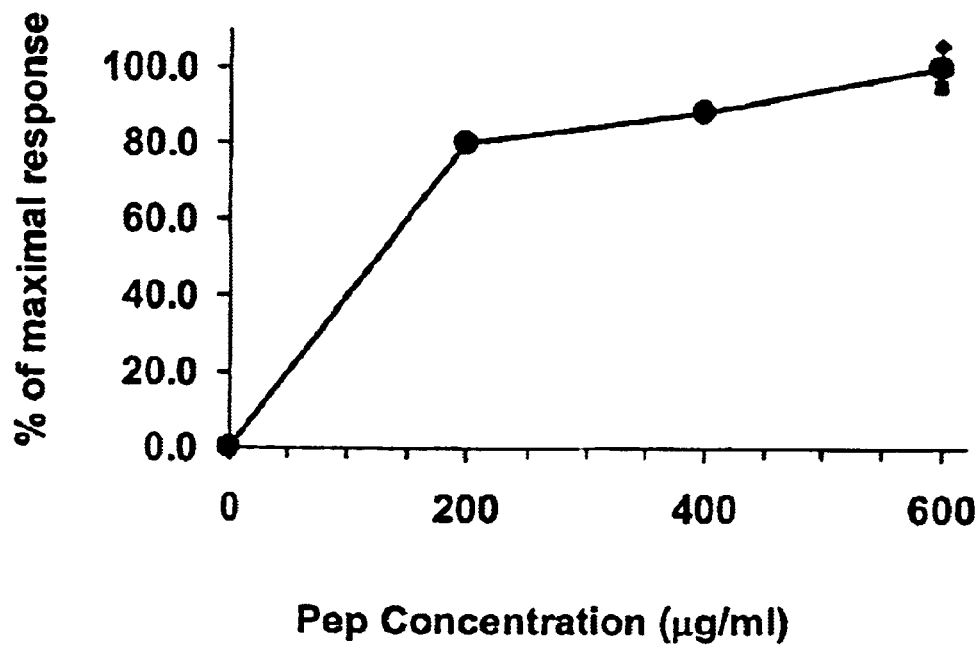
FIG. 6 is a graph of the dose response of peptide WALL005 (6a) on histamine secretion; and (6b) on compound 48/80 induced histamine release from intact mast cells.
Figure 6B:
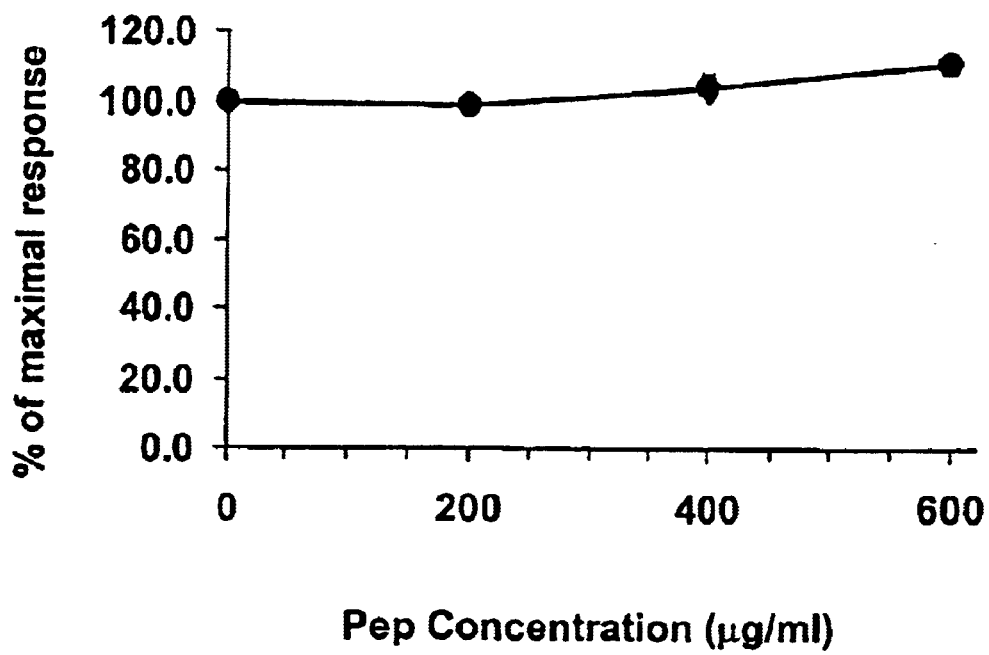

Incubation of purified intact mast cells in vitro with increasing concentrations of peptide WALL005 resulted in histamine secretion (FIG. 6A). These results have indicated that peptide WALL005 is likely to cause allergic side effects. Next, this peptide was tested for its ability to inhibit histamine secretion induced by compound 48/80. For this purpose, mast cells were incubated with increasing concentrations of the peptide, prior to their trigger with compound 48/80. As shown in FIG. 6B, peptide WALL005 had no effect on compound 48/80 induced histamine secretion. These results indicate that replacement of the tyrosine residue at the C-terminus with para-amino-F interferes with the activity of the peptide. Since peptide WALL005 had severe solubility problems, peptide aggregation may have accounted for the observed effects. Therefore, the activity of the succinylated form of this peptide was tested as well.

7) Peptide WALL014: Succinyl-AAVALLPAVLLALLAPKNNLKECGL-para-amino-F (SEQ ID NO:19)

Peptide WALL014 is identical to peptide WALL005 except for an additional Succinyl group at the N-terminus.

Figure 7A:
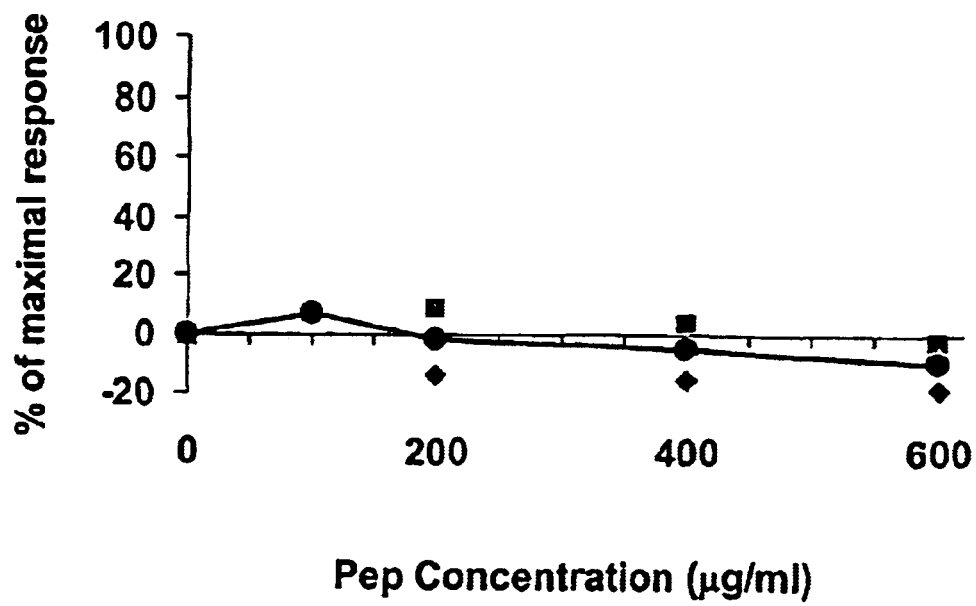
FIG. 7 is a graph of the dose response of peptide WALL014 (7a) on histamine secretion; and (7b) on compound 48/80 induced histamine release from intact mast cells.
Figure 7B:
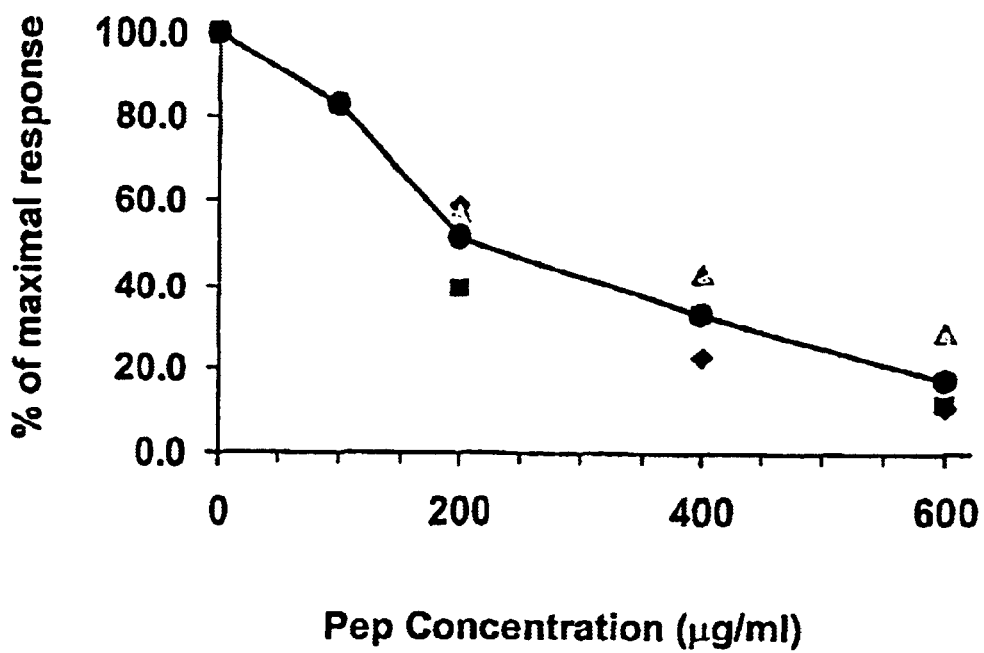

Incubation of purified intact mast cells in vitro with increasing concentrations of peptide WALL014 did not result in histamine secretion (FIG. 7A). These results have indicated that peptide WALL014 is unlikely to cause allergic side effects. Next, this peptide was tested for its ability to inhibit histamine secretion induced by compound 48/80. For this purpose, mast cells were incubated with increasing concentrations of the peptide, prior to their trigger with compound 48/80. As shown in FIG. 7B, peptide WALL014 blocked compound 48/80 induced histamine secretion in a dose dependent manner, with $IC_{50}$ values of 230 µg/ml and maximal inhibition of 83% at concentration of 600 µg/ml.

These results indicate that a soluble peptide, in which the Tyrosine residue at the C-terminal position 26 was replaced with para-amino-F, maintains its biological activity, that is to block histamine release induced by c48/80 and it has no side effects by itself.

These results may suggest that maintaining the biological activity of the peptide requires a C-terminal amino acid which includes an aromatic ring and a hydrogen bond forming head group.

8) Peptide WALL007: AAVALLPAVLLALLAP-KNNLKEVGLY (SEQ ID NO:12)

Figure 8A:
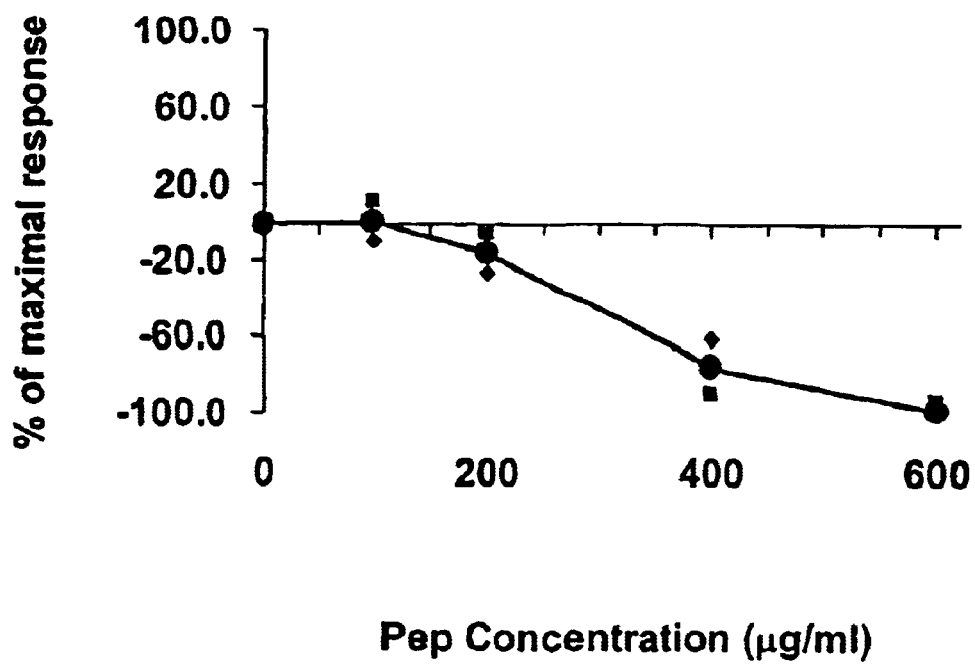
FIG. 8 is a graph of the dose response of peptide WALL007 (8a) on histamine secretion; and (8b) on compound 48/80 induced histamine release from intact mast cells.

Incubation of purified intact mast cells in vitro with increasing concentrations of Peptide WALL007 did not result in histamine secretion. In fact, incubation with the peptide resulted in inhibition of the basal level of histamine secretion, when compared to control cells (illustrated in FIG. 8A). These results have indicated that Peptide WALL007 is unlikely to cause allergic side effects. Next, this peptide was tested for its ability to block compound 48/80 induced histamine secretion. For this purpose, mast cells were incubated with increasing concentrations of the peptide, prior to their trigger with compound 48/80.

Figure 8B:
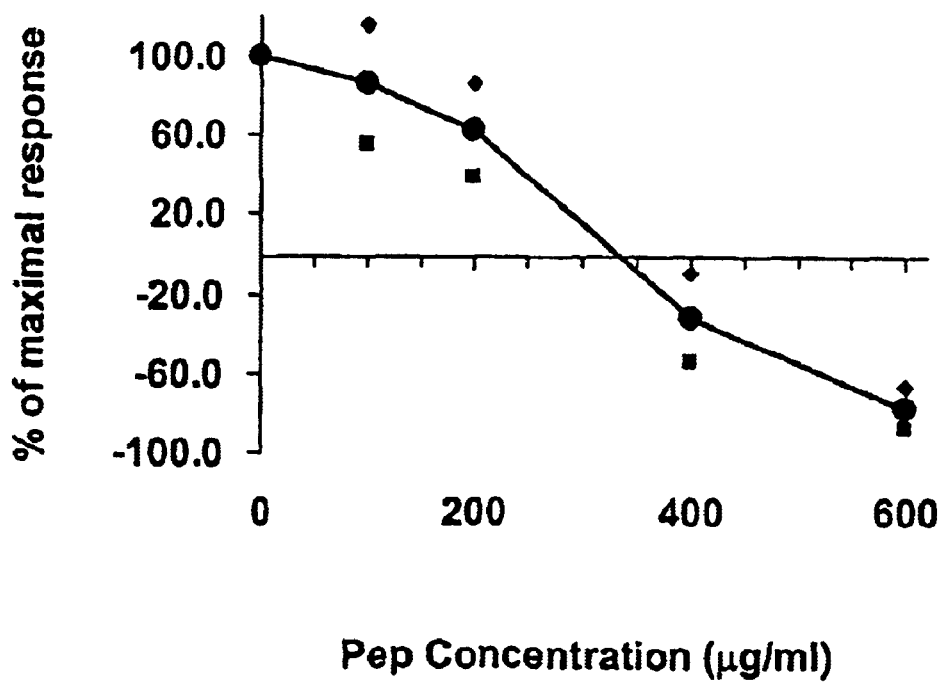

As shown in FIG. 8B peptide WALL007 blocked compound 48/80 induced histamine secretion in a dose dependent manner. A potent inhibition was already demonstrated at a concentration of 400 μg/ml, while maximal inhibition was demonstrated at a concentration of 600 μg/ml. Under these conditions, the level of histamine secretion was lower than the basal level of histamine secretion in control cells.

These results demonstrate that substitution of the cysteine residue at position 23 with valine, while reducing the risk of possible oxidation of the peptide, increases peptide efficacy. The $IC_{50}$ was reduced from 400 μg/ml for the unmodified peptide (Peptide 2 in Patent application WO 00/78346) to 230 μg/ml for peptide WALL007 as shown in FIG. 8B. Therefore peptide WALL007 (AAVALLPAVLLALLAPKNNLKEVGLY, (SEQ ID NO:12) is a novel potent inhibitor of mast cell degranulation.

From these results it would appear that the amino acid located at position 23 can be replaced by Valine demonstrating improved efficacy. However, we have previously shown that substitution of the cysteine residue with serine, that formed the sequence AAVALLPAVLLALLAP-KNNLKESGLY (SEQ ID NO:30), resulted in loss of activity of the entire peptide (Patent application WO 00/78346). Therefore, we claim that an active peptide, which inhibits mast cell degranulation, should contain at position 23 Cysteine or a stable isosteric residue which is not prone to oxidation or any chemical modification, such as Valine, as an essential condition for peptide activity 9) Peptide WALL016: Succinyl-AAVALLPAVLLALLAPKNNLKEVGLY (SEQ ID NO:21)

Figure 9A:
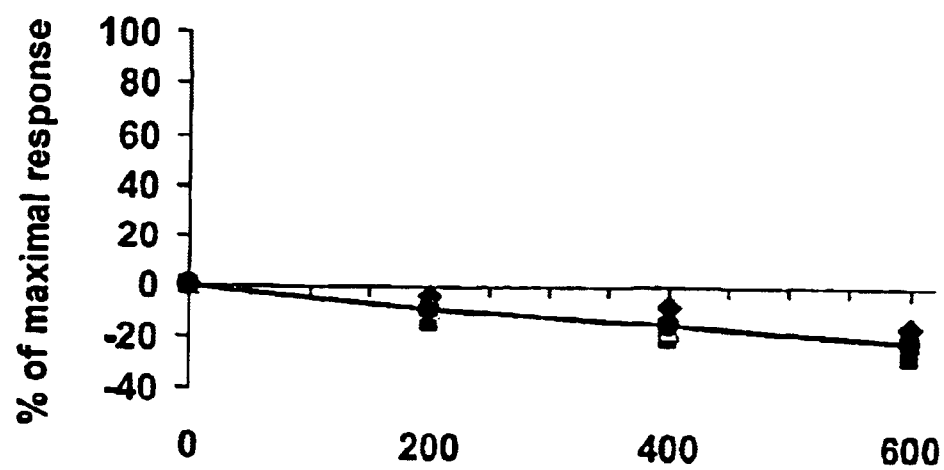
FIG. 9 is a graph of the dose response of peptide WALL016 (9a) on histamine secretion; and (9b) on compound 48/80 induced histamine release from intact mast cells.
Figure 9B:
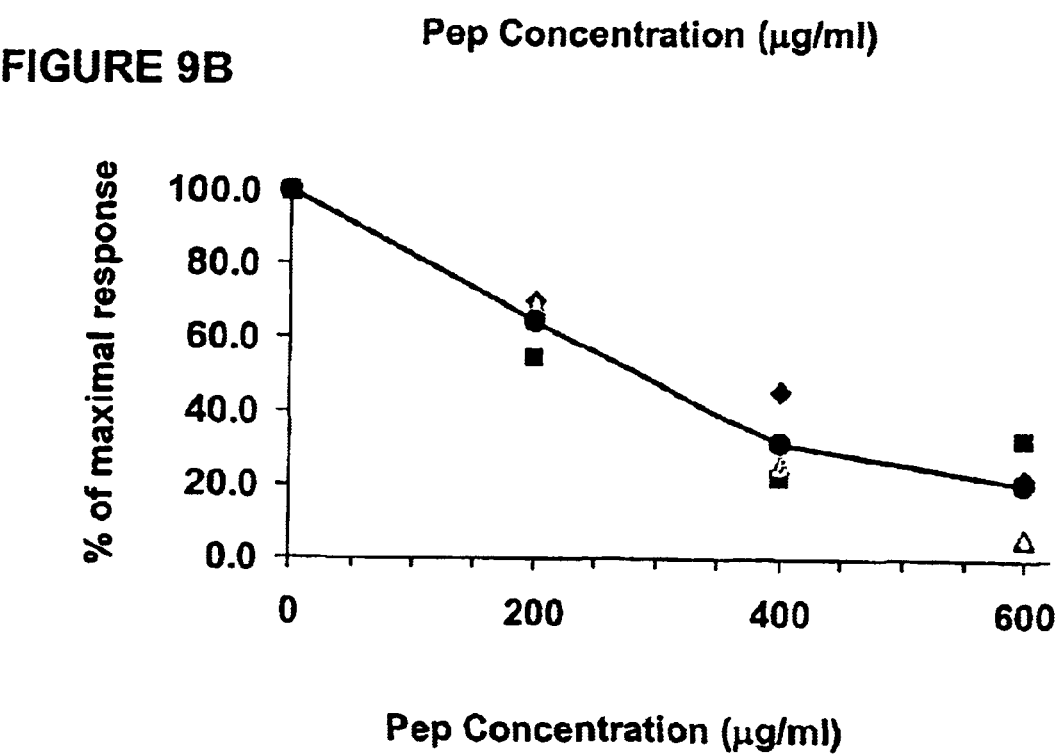

Incubation of purified intact mast cells in vitro with increasing concentrations of peptide WALL016 did not result in histamine secretion (FIG. 9A). In fact, incubation with the peptide resulted in inhibition of the basal histamine secretion, when compared to control cells (illustrated in FIG. 9A). These results have indicated that peptide WALL016 is unlikely to cause allergic side effects. Next, this peptide was tested for its ability to inhibit histamine secretion induced by compound 48/80. For this purpose, mast cells were incubated with increasing concentrations of the peptide, prior to their trigger with compound 48/80. As shown in FIG. 9B, peptide WALL016 blocked compound 48/80 induced histamine secretion in a dose dependent manner, with $IC_{50}$ values of 295 μg/ml and maximal inhibition of 79.6% at a concentration of 600 μg/ml.

These results indicate that replacement of the Cysteine residue at position 23 with valine, in conjunction with the addition of a succinyl residue at the N-terminus of the peptide, results in an active peptide demonstrating the ability to block histamine secretion from mast cells.

The next set of peptides were synthesized and analyzed in order to demonstrate the importance of the type of linkage which connects between the two segments of the complex peptide, that is the connection between the importation and the functional sequences. In particular, to assess the importance for biological activity of the proline residue as the point of junction between the importation segment and the functional moiety.

10) Peptide WALL004: AAVALLPAVLLAL-LAAKNNLKECGLY (SEQ ID NO:9)

Figure 10A:
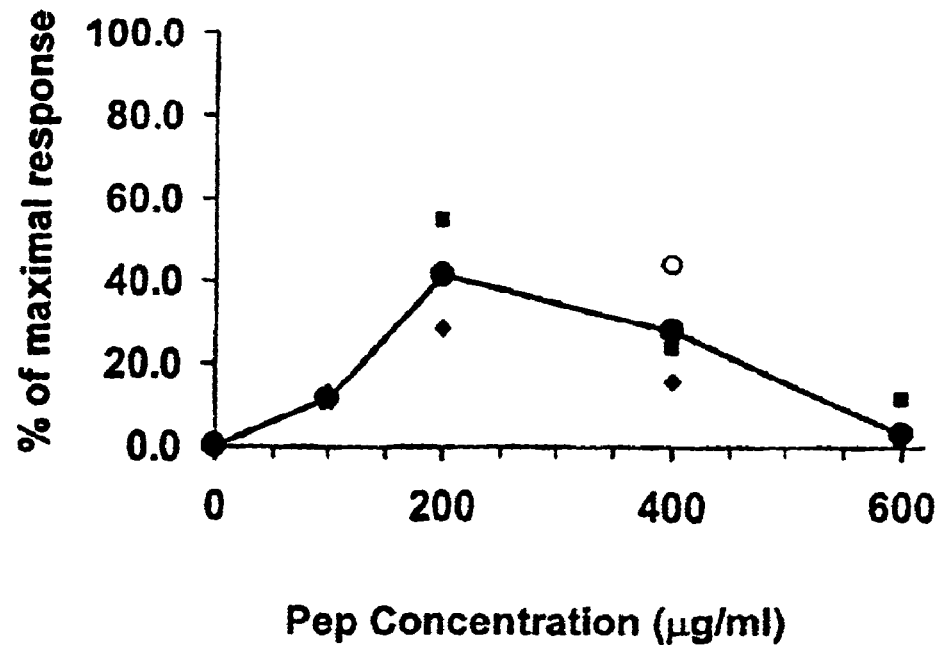
FIG. 10 is a graph of the dose response of peptide WALL004 (10a) on histamine secretion; and (10b) on compound 48/80 induced histamine release from intact mast cells.

Incubation of purified intact mast cells in vitro with increasing concentrations of Peptide WALL004 resulted in moderate histamine secretion, especially at a peptide concentration of exceeding 200 μg/ml (demonstrated in FIG. 10A). These results suggested that this peptide is likely to cause only minor or no allergic side effects and can therefore serve as a potential inhibitor of mast cell exocytosis.

The peptide was also tested for its ability to block compound 48/80 induced histamine secretion. Mast cells were incubated with increasing concentrations of the peptide, followed by induction of histamine secretion by compound 48/80.

Figure 10B:
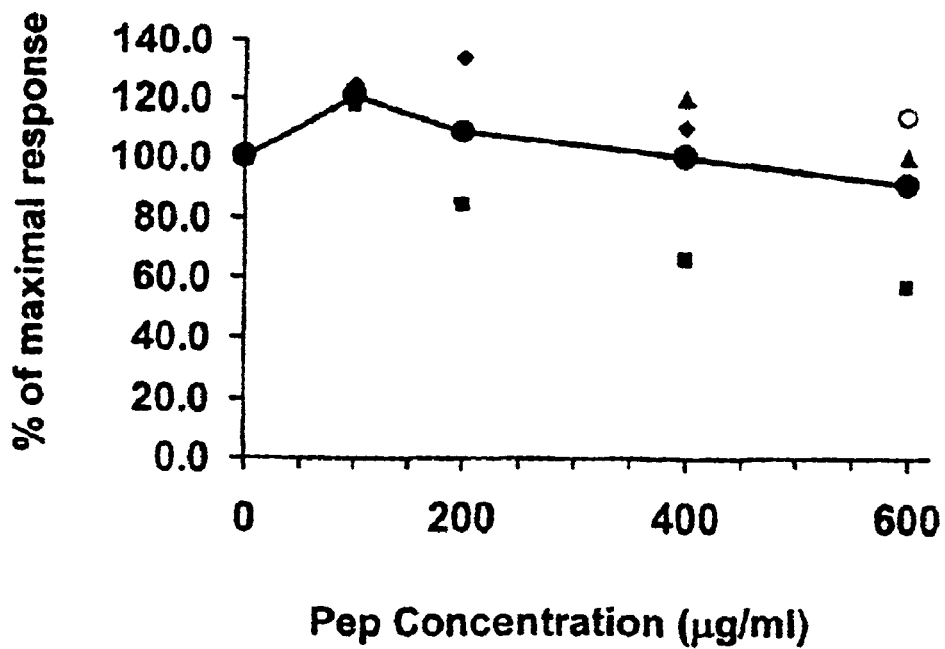

As shown in FIG. 10B, throughout the range of concentrations tested, peptide WALL004 failed to block histamine secretion induced by compound 48/80. These results demonstrate that substitution of the proline residue at position 16 with alanine caused a complete loss of the desired activity of the peptide. Therefore, we suggest that the amino acid proline, or any other natural or non-natural amino acid or covalent bond or moiety that would link covalently the importation segment (competent for cell penetration) with the functional segment (active in reducing or abolishing mast cell degranulation) in a manner, which gives rise to a bend or turn, is essential for the maintenance of the desired peptide activity. Examples include proline mimetics, N-alkylated or N-methylated amino acids at this position, double or triple bonds or the like.

In addition to proline, specific examples of moieties which induce suitable conformations include but are not limited to N-methyl amino acids such as sarcosine; hydroxy proline; anthranilic acid (2-amino benzoic acid); and 7-azabicycloheptane carboxylic acid.

11) Peptide WALL008: Succinyl-AAVALLPAVLLALLA-Sar-KNNLKECGLY (SEQ ID NO: 13)

Figure 11A:
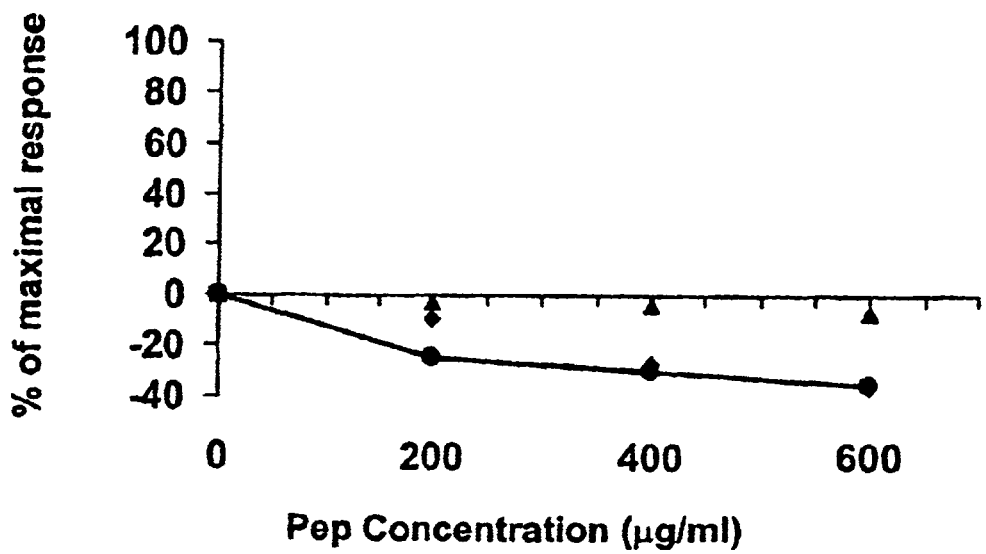
FIG. 11 is a graph of the dose response of peptide WALL008 (11a) on histamine secretion; and (11b) on compound 48/80 induced histamine release from intact mast cells.
Figure 11B:
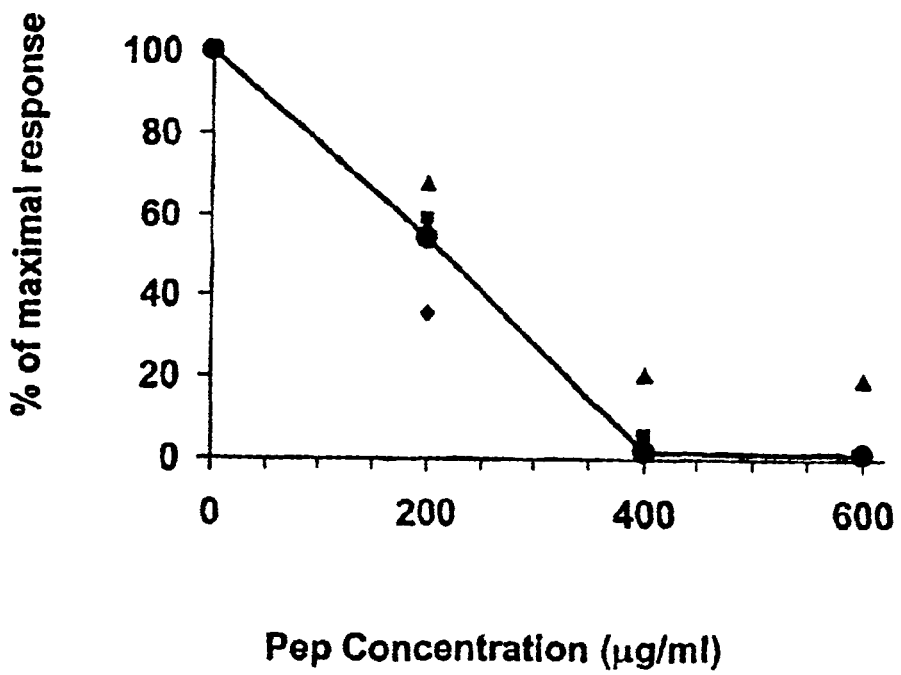

Incubation of purified intact mast cells in vitro with increasing concentrations of peptide WALL008 did not result in histamine secretion. In fact, incubation with the peptide resulted in inhibition of the basal level of histamine secretion, when compared to control cells (illustrated in FIG. 11A). These results have indicated that peptide WALL008 is unlikely to cause allergic side effects. Next, this peptide was tested for its ability to block compound 48/80 induced histamine secretion. For this purpose, mast cells were incubated with increasing concentrations of the peptide, prior to their trigger with compound 48/80. As shown in FIG. 11B, peptide WALL008 blocked compound 48/80 induced histamine secretion in a dose dependent manner, with $IC_{50}$ values at concentration of 220 µg/ml and maximal inhibition of 98.7% at concentration of 600 µg/ml.

These results demonstrate that substitution of the proline residue at position 16 in the peptide sequence with sarcosine, which, like the proline residue, introduces a conformational constraint in the peptide backbone, results in an active peptide, which inhibits histamine secretion from isolated mast cells.

12) Peptide WALL009: VTVLALGALAGVGVGKNNLKECGLY (SEQ ID NO:14)

Figure 12A:
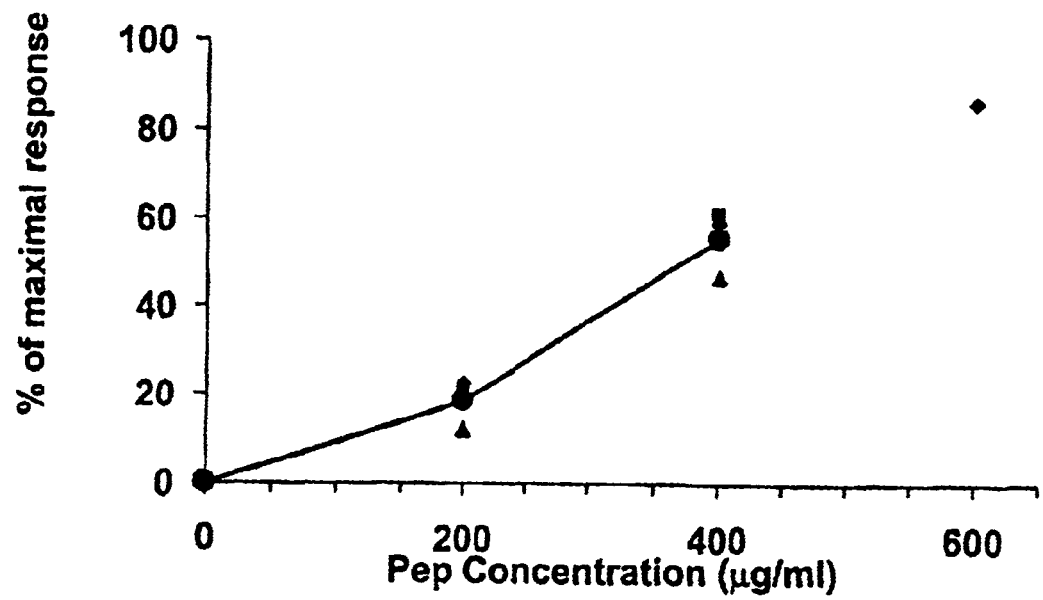
FIG. 12 is a graph of the dose response of peptide WALL009 (12a) on histamine secretion; and (12b) on compound 48/80 induced histamine release from intact mast cells.
Figure 12B:
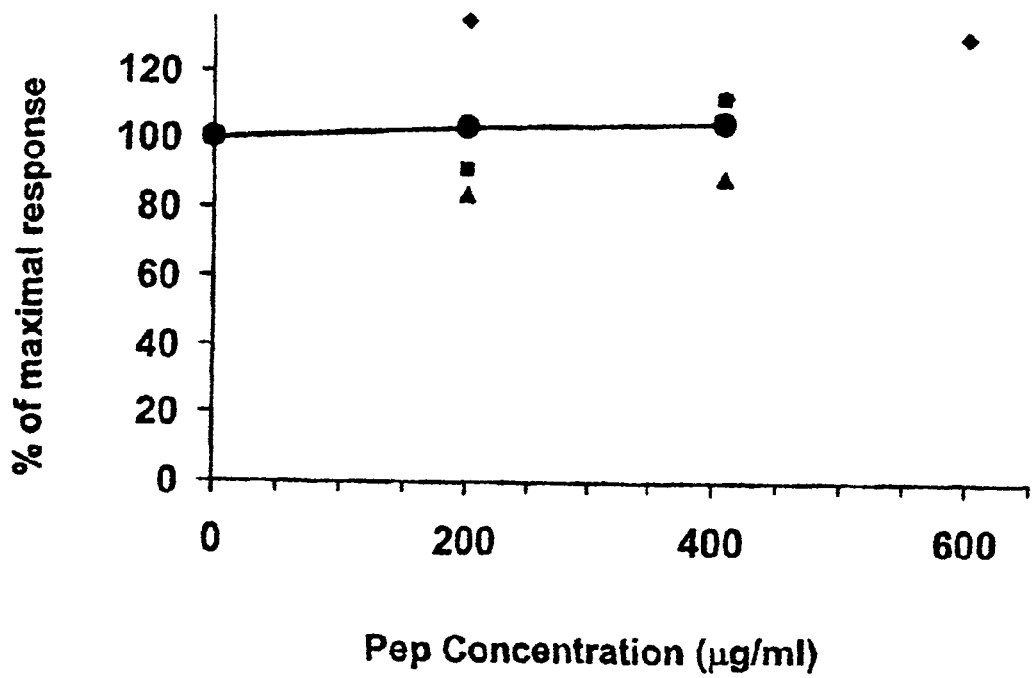

Incubation of purified intact mast cells in vitro with increasing concentrations of peptide WALL009 resulted in histamine secretion as a function of the peptide concentration (FIG. 12A). These results have indicated that peptide WALL009 is a potent secretagogue of mast cells which is likely to cause allergic side effects. This peptide was also tested for its ability to block compound 48/80-induced histamine secretion. For this purpose, mast cells were incubated with increasing concentrations of the peptide, prior to their trigger with compound 48/80. As shown in FIG. 12B, peptide WALL009 did not inhibit histamine release, induced by compound 48/80.

These results confirm our previous results (peptide 1 in WO 00/78346) demonstrating that peptide WALL009, which includes the leader motif of the signal sequence within human integrin β3, and the C-terminal sequence of Gαi$_3$, with no proline residue linking these two parts is inactive.

13) Peptide WALL010: VTVLALGALAGVGVGP-KNNLKECGLY (SEQ ID NO:15)

Figure 13A:
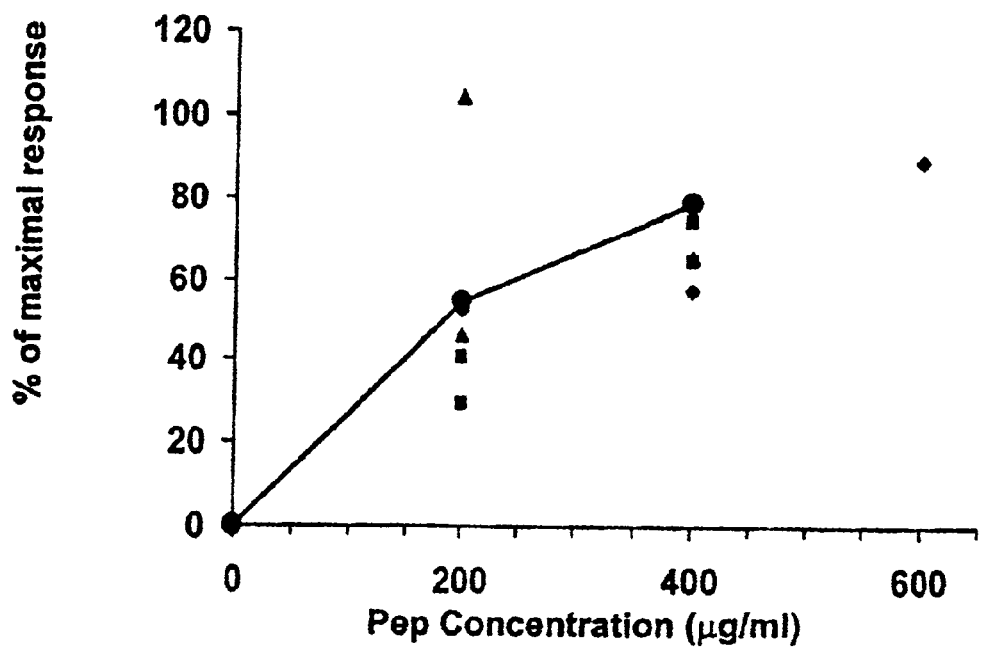
FIG. 13 is a graph of the dose response of peptide WALL010 (13a) on histamine secretion; and (13b) on compound 48/80 induced histamine release from intact mast cells.
Figure 13B:
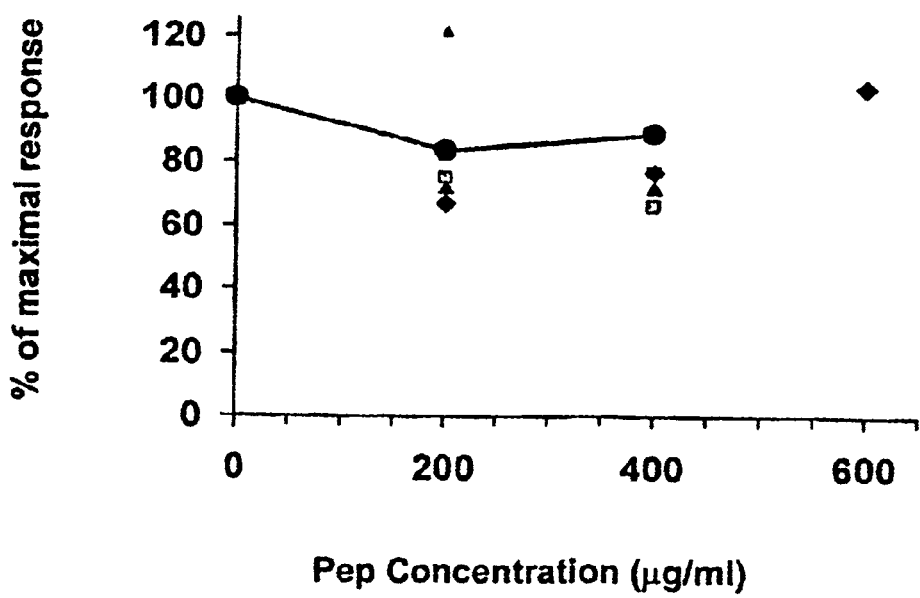

Incubation of purified intact mast cells in vitro with increasing concentrations of peptide WALL010 resulted in histamine secretion as a function of peptide concentration (FIG. 13A). These results have indicated that peptide WALL010 is a potent secretagogue of mast cells and is therefore likely to cause allergic side effects. Next, this peptide was tested for its ability to block compound 48/80 induced histamine secretion. For this purpose, mast cells were incubated with increasing concentrations of the peptide, prior to their trigger with compound 48/80. As shown in FIG. 13B, peptide WALL010 did demonstrate a mild inhibition of histamine release, induced by compound 48/80, with maximal inhibition of 16.7% at a concentration of 200 µg/ml.

These results demonstrate that the addition of the proline residue, at the point of junction between the importation segment and the functional moiety has succeeded in converting an inactive peptide (WALL009), which by itself exhibited mast cell secretagogue activity, into an active peptide capable of inhibiting histamine secretion induced by compound 48/80. In this case the ability of the active sequence to inhibit histamine secretion, might be masked by the secretagogue activity of the leader sequence (as demonstrated in peptide WALL010), therefore resulting in only mild inhibition and efficacy. Nevertheless, it is evident that the addition of the proline residue at the point of linkage between the importation segment and the functional segment resulted in a significant shift in the peptide activity from a potent mast cell secretagogue into an inhibitor of histamine secretion.

14) Peptide WALL023: AAVALLPAVLLALLAPY-LGCEKLNNK (SEQ ID NO:22)

Figure 14:
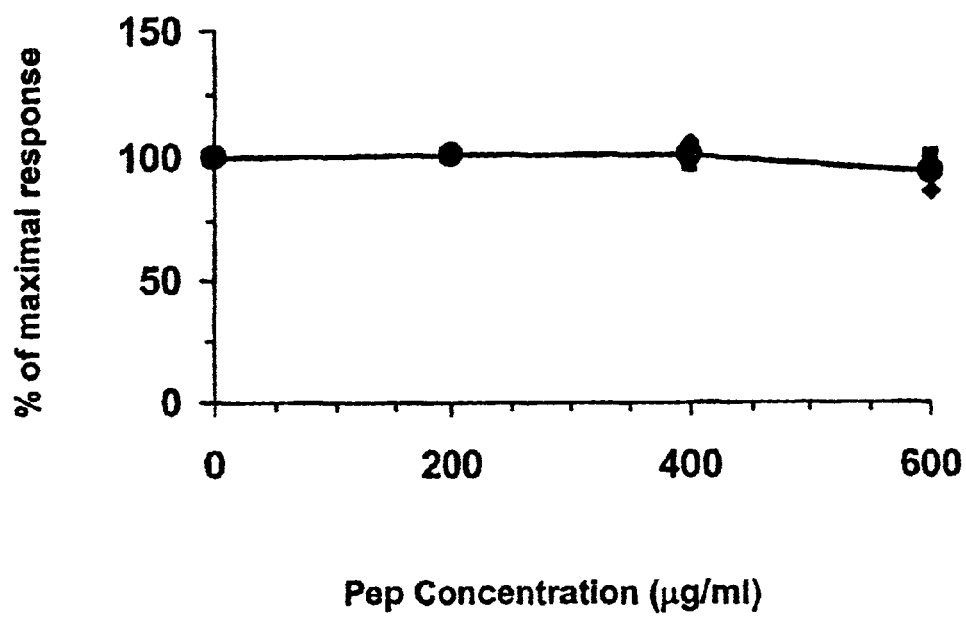
FIG. 14 is a graph of the dose response of peptide WALL023 on compound 48/80 induced histamine release from intact mast cells.

Incubation of purified intact mast cells in vitro with 600 µg/ml of peptide WALL023 did not result in histamine secretion. These results have indicated that peptide WALL023 is unlikely to cause allergic side effects. Next, this peptide was tested for its ability to inhibit histamine secretion induced by compound 48/80. For this purpose, mast cells were incubated with increasing concentrations of the peptide, prior to their being triggered with compound 48/80. As shown in FIG. 14, peptide WALL023 had no effect on compound 48/80 induced histamine secretion.

These results indicate that the peptide that comprises the non-active sequence of Gi$_3$ (anti-sense sequence) is not able to inhibit the histamine secretion induced by compound 48/80, indicating that blocking the histamine release, induced by compound 48/80 is specific and is dependent on Gi$_3$ activation.

15) Inhibition of Late Phase Inflammatory Responses Via Protein Kinases

Figure 15A:
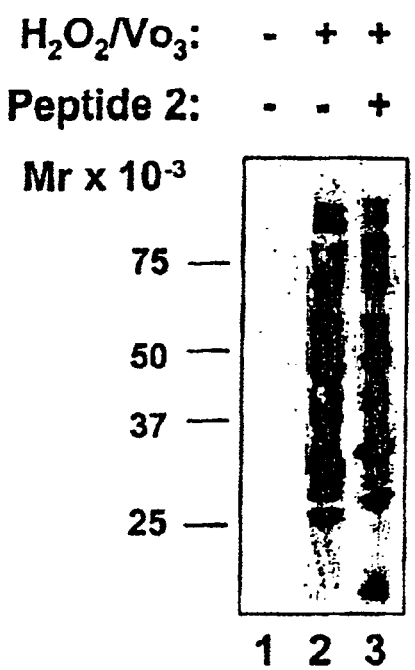
FIG. 15 demonstrates protein tyrosine kinase (PTK) activation induced by compound 48/80 (15A) or $H_2O_2/VO_3$ (15B), followed by treatment with peptide 2.
Figure 15B:
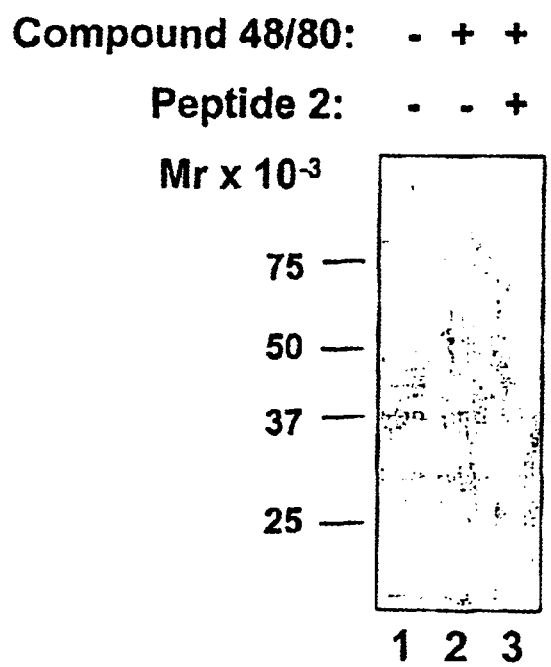
Figure 16A:
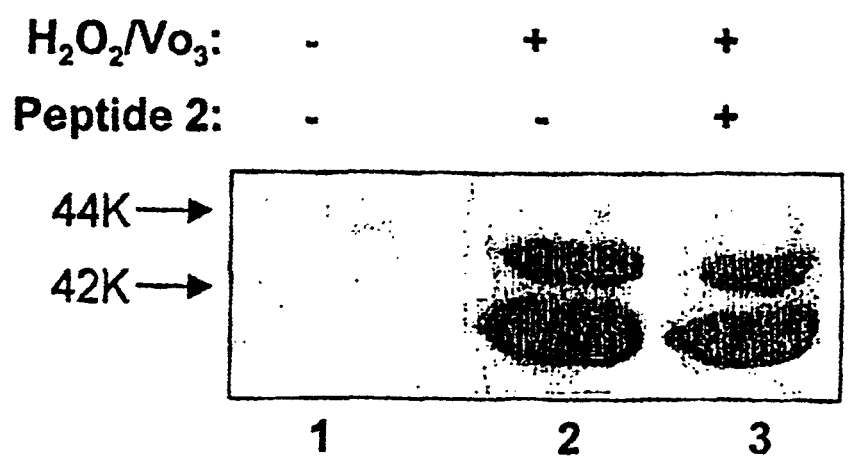
FIG. 16 demonstrates mitogen activated protein kinase (MAPK) activation induced by compound 48/80 (16A) or $H_2O_2/VO_3$ (16B), followed by treatment with peptide 2.
Figure 16B:
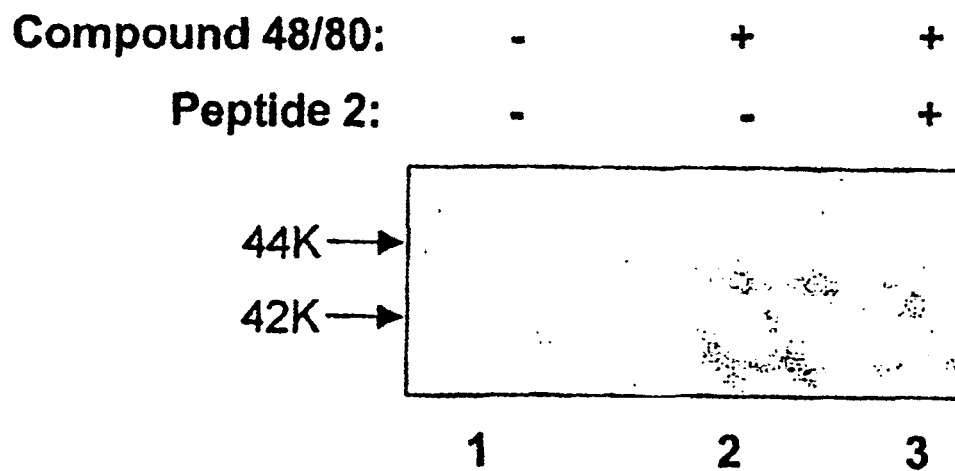

Experiments were conducted in order to demonstrate specific inhibition by peptides of the invention of protein tyrosine kinases (PTKs) and the Mitogen-activated protein kinases (MAPKs) activation after exposure to basic secretagogues. Purified intact mast cells were incubated with 600 µg/ml of peptide 2 and the activation of protein tyrosine kinase (PTK) and Mitogen-activated protein kinase (MAPK) was validated. The results demonstrate an inhibition by Peptide 2 of PTKs and MAPKs activation induced by compound 48/80 (FIG. 15A and 16A), a basic secretagogue that activates directly the pertussis toxin sensitive Gi$_3$. In contrast, peptide 2 did not inhibit the activation of protein tyrosine kinases and MAPKs induced by $H_2O_2/VO_3$ (FIG. 15B, and 16B) that stimulates protein tyrosine phosphorylation in a pertussis toxin insensitive fashion by inhibiting protein tyrosine phosphatases.

These results indicate that peptide 2 inhibits, in addition to histamine release, the activation of PTKs and MAPKs induced by basic secretagogues. Activation of these protein kinases was demonstrated previously as a crucial event, leading to activation of the late phase inflammatory reaction such as synthesis de novo of leukotrienes and prostaglandins. Therefore, our results indicate that this peptide inhibited also the pathway that contributes to the de novo production of inflammatory mediators such as leukotrienes and prostaglandins. We have also demonstrated that peptide 2 inhibited a specific pertussis toxin sensitive activation of PTKs and MAPKs that can be dependent on Gi$_3$ activation.

The aforementioned results, demonstrated by peptides WALL004, WALL008, WALL009 and WALL010 confirm that the linker is a crucial element of the present invention, whereby the linker must impose conformational constraints at or near the junction of the two segments of the molecule to yield a biologically active entity. Therefore, the first segment must be connected to the second segment through a linker or a direct bond, whereby the linker creates a conformational constraint, by forming a bend or turn. Examples include but are not limited to, residues such as proline, or proline mimetic or N-methyl amino acids such as sarcosine or any other moiety which introduces a rigid bend into the peptide backbone.

Table 1 summarizes the results obtained in the in vitro system.

TABLE 1

Summary of in vitro experiments monitoring histamine secretion from isolated mast cells, following incubation with the following peptides

| Peptide | Sequence | Secreta-gogue* | Inhibitor** | $IC_{50}$ ($\mu$g/ml) | Remarks |
|---|---|---|---|---|---|
| WALL006 | AAVALLPAVLLALLAPKQNLKECGLY (SEQ ID NO:11) | − | + | 560 | solubility problem |
| WALL015 | Succinyl-AAVALLPAVLLALLAPKQNLKECGLY (SEQ ID NO:20) | − | ++ | 300 | Good solubility |
| WALL011 | Succinyl-AAVALLPAVLLALLAPKSNLKECGLY (SEQ ID NO:16) | − | +++ | 160 | Good solubility |
| WALL012 | Succinyl-AAVALLPAVLLALLAPKENLKECGLY (SEQ ID NO:12) | − | +++ | 320 | Good solubility |
| WALL013 | Succinyl-AAVALLPAVLLALLAPKANLKECGLY | − | +++ | 245 | Good solubility |
| WALL005 | AAVALLPAVLLALLAPKNNLKECGL-para-amino-F (SEQ ID NO:10) | + | − | — | Solubility problem |
| WALL014 | Succinyl-AAVALLPAVLLALLAPKNNLKECGL-para-amino-F (SEQ ID NO:19) | − | +++ | 230 | Good solubility |
| WALL007 | AAVALLPAVLLALLAPKNNLKEVGLY (SEQ ID NO:12) | − | +++ | 230 | Solubility problem |
| WALL016 | Succinyl-AAVALLPAVLLALLAPKNNLKEVGLY (SEQ ID NO:21) | − | ++ | 295 | Good solubility |
| WALL004 | AAVALLPAVLLALLAAKNNLKECGLY (SEQ ID NO:9) | −/+ | − | — | Solubility problem |
| WALL008 | Succinyl-AAVALLPAVLLALLA-Sar-KNNLKECGLY (SEQ ID NO:13) | − | +++ | 220 | Good solubility |
| WALL009 | VTVLALGALAGVGVGKNNLKECGLY (SEQ ID NO:14) | + | − | — | Good solubility |
| WALL010 | VTVLALGALAGVGVGPKNNLKECGLY (SEQ ID NO:15) | + | −/+ | — | Good solubility |
| WALL023 | AAVALLPAVLLALLAPYLGCEKLNNK (SEQ ID NO:22) | − | − | — | Good solubility |

*Histamine secretion following incubation of mast cell with different concentrations of each peptide: − No side effect of histamine secretion. + Peptide that induce histamine secretion (Secretagogue).
**Extent of inhibition of histamine secretion from mast cells, followed by incubation with different concentrations of each peptide and induction of the allergic reaction. +++ Potent inhibitor ($\geq$80% inhibition), ++ Moderate inhibitor (50%–70% inhibition), + Poor inhibitor ($\leq$50% inhibition), − No inhibition.

EXAMPLE 3

Testing the Effects of the Treatment of the Present Invention in vivo

The ability of peptides according to the present invention to block allergic reaction in vivo was tested on the skin of rats by using compound 48/80 as the allergen. Peptides WALL007, WALL008, WALL012, WALL013, WALL014, WALL015 and WALL016 that were demonstrated to be effective in vitro, are shown to effectively block the allergic response in vivo.

WALL007: AAVALLPAVLLALLAPKNNLKEVGLY (SEQ ID NO:12)
WALL008: Succinyl-AAVALLPAVLLALLA-Sar-KNNLKECGLY (SEQ ID NO:13)
WALL012: Succinyl-AAVALLPAVLLALLAPKENLKECGLY (SEQ ID NO:17)
WALL013: Succinyl-AAVALLPAVLLALLAPKANLKECGLY (SEQ ID NO:18)
WALL014: Succinyl-AAVALLPAVLLALLAPKNNLKECGL-para-amino-F (SEQ ID NO:18)
WALL015: Succinyl-AAVALLPAVLLALLAPKQNLKECGLY (SEQ ID NO:20)
WALL016: Succinyl-AAVALLPAVLLALLAPKNNLKEVGLY (SEQ ID NO:21)

The experimental method is described below.

Materials and Methods

The hair of the abdominal area of CR rats was carefully removed with an electric clipper and a depilatory cream. In each animal the abdominal area was divided to six equal zones that were marked by pen. Each zone was either subjected to peptide treatment or served as a control. The peptide was injected intradermally as follows: 20 μl of peptide solution at different concentrations (dissolved in 10% DMSO in DDW) were injected intradermally to an indicated abdominal area using a 27-gauge sterile needle.

Skin tests were performed 0.5, or 1 hour following application of the peptide. Skin tests were performed by injecting intradermally 20 μl of the allergen (0.1 mg/ml compound 48/80 dissolved in DDW) or DDW alone (Vehicle), into the center of each marked area on the abdominal skin using a 27-gauge sterile needle. The allergic response was monitored by outlining with a marker the wheals which developed in response to allergen or vehicle treatment.

To quantitate the skin test results, the marker signs were transferred onto paper with scotch tape. The areas of the wheals were outlined and calculated by a computerized software (NIH-Image).

Experimental Results

The area of the wheals which developed in response to topical application of the test peptide followed by compound 48/80 or saline injection are recorded.

Tables 2–8 presents the mean areas of the wheals, which developed in response to intradermal injection of each of the tested peptides, followed by either compound 48/80 or DDW injection applied after 0.5 or 1 hour. Two doses were tested for each peptide—20 and 200 μg (injection of 20 μl from a stock solution of 1 mg/ml or 10 mg/m respectively). Mean wheal areas were calculated for each treatment and the significance of the results was determined using student's T-test.

Table 2 The results presented in Table 2 demonstrate that intradermal injection of Peptide WALL007 reduced the allergic reaction in a dose dependent manner, reaching significant inhibition when administered 0.5 or 1 hour before the allergic induction. These results therefore indicate that Peptide WALL007 has the potential to block allergic reactions in vivo Table 3 The results presented in Table 3 demonstrate that intradermal injection of Peptide WALL016 reduced compound 48/80 induced allergic reaction in a dose dependent manner, reaching significant inhibition at both 0.5 and 1 hour before the allergic induction. These results therefore indicate that Peptide WALL0016 has the potential to block allergic reactions in vivo.

Table 4 The results presented in Table 4 demonstrate that intradermal injection of Peptide WALL008 reduced the allergic reaction in a dose dependent manner, reaching significant inhibition at 0.5 hour before the allergic induction. These results therefore indicate that Peptide WALL008 has the potential to block allergic reactions in vivo. .

Table 5 The results presented in Table 5 demonstrate that intradermal injection of Peptide WALL012 reduced compound 48/80-induced allergic reactions in a dose dependent manner, reaching significant inhibition at 0.5 hour before the allergic induction. Therefore, Peptide WALL012 has the potential to block allergic reactions in vivo.

Table 6 The results presented in Table 6 demonstrate that intradermal injection of Peptide WALL013 significantly reduced compound 48/80-induced allergic reaction at concentrations of 1 mg/ml and 10 mg/ml, when applied 0.5 hour before induction of the allergic reaction. Peptide WALL013 therefore has the potential to block allergic reactions in vivo.

A representative experiment (depicted in Table 7) demonstrates that intradermal injection of Peptide WALL015 blocked compound 48/80-induced allergic reaction in vivo. Peptide WALL015 reduced the allergic reaction at concentration of 1 and 10 1 and 10 mg/ml , when applied 0.5 hour before induction of the allergic induction.

The results presented in Table 8 demonstrate that intradermal injection of Peptide WALL014 significantly reduced the allergic reaction evoked by compound 48/80 at a concentration of 1 mg/ml, when applied 0.5 hour before induction of the allergic reaction. In contrast, when applied 1 hour before compound 48/80, no significant inhibition was demonstrated (data not shown). Peptide WALL014 therefore has the potential to block allergic reactions in vivo.

It is noteworthy that intradermal injection of each peptide alone exerted no stimulatory effect on the cutaneous allergic reactions, thus indicating that each compound by itself is not allergenic (see Tables 2–8).

TABLE 2

Mean Wheal Area (mm$^2$ ± STD) in Response to Intradermal Injection of Peptide WALL007 followed by compound 48/80.

| | Peptide Concentration (mg/ml) | | |
|---|---|---|---|
| | 0 | 1 | 10 |
| A. Intradermal injection of Peptide WALL007, 0.5 hour before allergic induction | | | |
| Vehicle | 74.5 ± 18.0 | 76.5 ± 14.1 | 74.5 ± 26.4 |
| | (n = 12) | (n = 12) | (n = 12) |
| Compound 48/80 | 141.4 ± 29.7 | 116.2 ± 22.8* | 99.0 ± 32.4** |
| | (n = 12) | (n = 12) | (n = 12) |
| B. Intradermal injection of Peptide WALL007, 1 hour before allergic induction | | | |
| Vehicle | 67.5 ± 20.5 | 62.4 ± 11.1 | 65.9 ± 10.0 |
| | (n = 14) | (n = 15) | (n = 11) |
| Compound 48/80 | 113.4 ± 30.5 | 86.7 ± 21.8** | 95.4 ± 21.2* |
| | (n = 14) | (n = 15) | (n = 12) |

*p < 0.05 as compared to positive control group (Compound 48/80).
**p < 0.01 as compared to positive control group (Compound 48/80)
All vehicle groups are significantly different form the positive control groups (Compound 48/80, p < 0.01)

TABLE 3

Mean Wheal Area (mm$^2$ ± STD) in Response to Intradermal Injection of Peptide WALL016 followed by compound 48/80.

| | Peptide Concentration (mg/ml) | | |
|---|---|---|---|
| | 0 | 1 | 10 |
| A. Intradermal injection of Peptide WALL016, 0.5 hour before allergic induction | | | |
| Vehicle | 88.2 ± 19.6 | 66.4 ± 12.5 | 72.6 ± 16.2 |
| | (n = 5) | (n = 5) | (n = 5) |
| Compound 48/80 | 142.6 ± 39.3 | 104.2 ± 21.6* | 1.2 ± 7.9** |
| | (n = 5) | (n = 5) | (n = 5) |
| B. Intradermal injection of Peptide WALL016, 1 hour before allergic induction | | | |
| Vehicle | 79.3 ± 24.3 | 62.8 ± 14.6 | 69.3 ± 17.0 |
| | (n = 6) | (n = 6) | (n = 6) |
| Compound 48/80 | 151.4 ± 17.0 | 96.3 ± 15.6** | 82.1 ± 27.2** |
| | (n = 6) | (n = 6) | (n = 6) |

*p < 0.05 as compared to positive control group (Compound 48/80).
**p < 0.01 as compared to positive control group (Compound 48/80).
All Vehicle groups are significantly different form the positive control groups (Compound 48/80) at 0.5 hour - p < 0.05, and at 1 hour - p < 0.01.

TABLE 4

Mean Wheal Area (mm$^2$ ± STD) in Response to Intradermal Injection of Peptide WALL008 followed by compound 48/80. Intradermal injection of Peptide WALL008, 0.5 hour before allergic induction

| | Peptide Concentration (mg/ml) | | |
|---|---|---|---|
| | 0 | 1 | 10 |
| Vehicle | 63.7 ± 16.8 | 79.9 ± 22.3 | 72.8 ± 13.6 |
| | (n = 4) | (n = 4) | (n = 4) |

TABLE 4-continued

Mean Wheal Area (mm² ± STD) in Response to Intradermal Injection of Peptide WALL008 followed by compound 48/80. Intradermal injection of Peptide WALL008, 0.5 hour before allergic induction

| | Peptide Concentration (mg/ml) | | |
|---|---|---|---|
| | 0 | 1 | 10 |
| Compound 48/80 | 128.0 ± 5.7 (n = 4) | 104.1 ± 18.5* (n = 4) | 73.7 ± 12.2** (n = 4) |

*$p < 0.05$ as compared to positive control group (Compound 48/80).
**$p < 0.01$ as compared to positive control group (Compound 48/80)
All vehicle groups are significantly different form the positive control groups (Compound 48/80, $p < 0.01$).

TABLE 5

Mean Wheal Area (mm² ± STD) in Response to Intradermal Injection of Peptide WALL0012 followed by compound 48/80. Intradermal injection of Peptide WALL012, 0.5 hour before allergic induction

| | Peptide Concentration (mg/ml) | | |
|---|---|---|---|
| | 0 | 1 | 10 |
| Vehicle | 70.0 ± 13.7 (n = 5) | 71.6 ± 13.8 (n = 5) | 66.7 ± 10.1 (n = 5) |
| Compound 48/80 | 128.1 ± 14.5 (n = 5) | 104.8 ± 12.6* (n = 5) | 75.1 ± 8.5 (n = 5)** |

*$p < 0.05$ as compared to positive control group (Compound 48/80).
**$p < 0.01$ as compared to positive control group (Compound 48/80)
All vehicle groups are significantly different form the positive control groups (Compound 48/80, $p < 0.01$)

TABLE 6

Mean Wheal Area (mm² ± STD) in Response to Intradermal Injection of Peptide WALL013 followed by compound 48/80. Intradermal injection of Peptide WALL013, 0.5 hour before allergic induction

| | Peptide Concentration (mg/ml) | | |
|---|---|---|---|
| | 0 | 1 | 10 |
| Vehicle | 72.4 ± 16.2 (n = 4) | 4.7 ± 12.0 (n = 4) | 77.3 ± 13.5 (n = 4) |
| Compound 48/80 | 146.4 ± 28.5 (n = 4) | 9.7 ± 13.7 (n = 4)** | 96.4 ± 28.4 (n = 4)* |

*$p < 0.05$ as compared to positive control group (Compound 48/80).
**$p < 0.01$ as compared to positive control group (Compound 48/80)
All vehicle groups are significantly different form the positive control groups (Compound 48/80, $p < 0.01$).

TABLE 7

A Representative Experiment Demonstrating the Wheal Area (mm²) in Response to Intradermal Injection of Peptide WALL015 followed by compound 48/80. Intradermal injection of Peptide WALL015, 0.5 hour before allergic induction

| | Peptide Concentration (mg/ml) | | |
|---|---|---|---|
| | 0 | 1 | 10 |
| Vehicle | 98.3 | 110.4 | 89.7 |
| Compound 48/80 | 151.5 | 100.1 | 75.3 |

TABLE 8

Mean Wheal Area (mm² ± STD) in Response to Intradermal Injection of Peptide WALL014 followed by compound 48/80. Intradermal injection of Peptide WALL014, 0.5 hour before allergic induction

| | Peptide Concentration (mg/ml) | | |
|---|---|---|---|
| | 0 | 1 | 10 |
| Vehicle | 96.6 ± 8.6 (n = 2) | 87.2 ± 1.9 (n = 2) | 100.1 ± 38.9 (n = 2) |
| Compound 48/80 | 153.7 ± 13.4 (n = 2) | 108.1 ± 15.0* (n = 2) | 91.5 ± 34.9 (n = 2) |

*$p < 0.05$ as compared to positive control group (Compound 48/80).

The in vivo results demonstrated above, further reinforce the in vitro results, demonstrating that the active peptides according to the invention have the potential to also block allergic reactions in vivo, such as the cutaneous allergic reactions.

EXAMPLE 4

Methods and Compositions for Administration

The peptides of the present invention, and their homologues or related compounds, hereinafter referred to as the "therapeutic agents of the present invention", can be administered to a subject by various routes of administration, which are well known in the art. Hereinafter, the term "therapeutic agent" includes a peptide as previously defined, in particular peptides exemplified herein and/or homologues, analogues or mimetics thereof, or any biologically active substance having a substantially similar effect as previously defined.

Hereinafter, the term "subject" refers to the human or lower animal to whom the therapeutic agent is administered. For example, administration may be done topically (including ophthalmically, vaginally, rectally, intranasally and by inhalation), orally, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the therapeutic agent. Persons of ordinary skill in the art can easily determine optimum dosages, dosing methodologies and repetition rates.

EXAMPLE 5

Method of Treatment of Allergic Conditions

As noted above, the therapeutic agents of the present invention have been shown to be effective inhibitors of the allergic process by blocking mast cell degranulation, thereby preventing and/or alleviating an allergenic condition. The following example is an illustration only of a method of treating an allergenic condition with the therapeutic agent of the present invention, and is not intended to be limiting.

The method includes the step of administering a therapeutic agent, in a pharmaceutically acceptable carrier as described in Example 4 above, to a subject to be treated. The therapeutic agent is administered according to an effective dosing methodology, preferably until a predefined endpoint is reached, such as the absence of a symptom of the allergenic condition in the subject, or the prevention of the appearance of such a symptom in the subject.

Allergic conditions for which the therapeutic agents of the present invention are useful include, but are not limited to, nasal allergy, irritation or allergic reactions in the eyes, allergic reactions in the skin including any type of allergen-induced rash or other skin irritation or inflammation, acute urticaria, psoriasis, psychogenic or allergic asthma, interstitial cystitis, bowel diseases, migraines, and auto-immune diseases such as multiple sclerosis.

EXAMPLE 6

Methods for Manufacturing the Therapeutic Complex of the Present Invention

The therapeutic complex of the present invention can be manufactured in various ways. For example, if the therapeutic complex includes a peptide for at least one the first segment and the second segment, or if the entire therapeutic complex is a peptide, then such a peptide could be manufactured by peptide synthetic methods which are well known in the art.

Alternatively, such a peptide could be produced by linking the signal sequence and the biologically active moiety through laboratory techniques for molecular biology which are well known in the art.

By way of illustration, as a non-limitative example, a recombinant fusion protein could be prepared which would feature the peptide permeabilization sequence in the N-terminus and the C-terminal moiety of $G\alpha_t$ or $G\alpha_{i3}$, preferably including the last 10 amino acids, for production in bacteria. For this purpose, DNA sequences coding for the desired peptides are amplified by PCR and purified. After sequence verification, these DNA sequences are ligated and cloned in an appropriate vector. The resulting recombinant plasmid is expressed in E. coli and the recombinant proteins purified from bacterial extracts.

EXAMPLE 7

Conformational Analysis and Computational Protocols

Conformation Sampling

As a full enumeration of all the possible conformations of a 10-residues peptide is impractical, a sampling procedure must be applied in order to generate a representative sample of the molecule's conformation space. Many methods are available for sampling molecular conformations, each harboring advantages and limitations. The sampling procedure adopted for the present study stems from the tendency to get the most stable conformation of a peptide at physiological pH with reasonable time. To accomplish this goal a two-step sampling procedure was applied. First, conformations are sampled from a high temperature molecular dynamics trajectory at 1000 K. Then each of the sampled high temperature conformations is gradually annealed down to 300 K using molecular dynamics. After the cooling step the energy of each conformation was quenched by direct minimization.

The annealed and minimized conformations constitute the conformation sample of that molecule. The gradual annealing guarantees that the resulting conformations will indeed be on the 300 K manifold (i.e., are accessible at 300 K), while the high temperature sampling allows us to cross high-energy barriers.

Technically, each sampling procedure starts with a 500 ps molecular dynamics trajectory at 1000 K (simulated using 2 fs timesteps). Conformations are sampled along the high temperature trajectory every 1 ps, resulting in a total of 500 conformations. Short molecular dynamic trajectories (simulated at 1 fs timesteps) are then applied to cool each of the high temperature conformations down to 300K (temperature decreases at 100 K steps). Following the cooling phase each structure is minimized by a combined protocol consisting of 200 Steepest Decent steps followed by Adopted Basis Newton-Raphson (ABNR) minimization until a total gradient of 0.01 is reached. The representation of the molecular dynamics and the various energy calculations were performed with the CHARMM program and the CHARMM all atom forcefield. No explicit water molecules were included, no energy cutoffs were applied and a distance dependent dielectric constant was used. In each conformational sample the conformation with the lowest energy was selected to represent the most stable conformation of the sequence.

Molecular Systems

Four 10-residues peptides analogs were studied. The peptides were with neutral N-terminal and with negative charge at the C-terminal. The initial conformations used in the sampling process of all peptides were the fully extended conformations. However, since the difference between peptide c and peptide b and between peptide d and peptide a is only in one residue an additional sampling was applied on peptides 3 and 4. These additional samplings for peptides c and d were based on the most stable conformation of peptides b and a, respectively.

Peptide a ($G\alpha i_3$): $NH_2$-Lys-Asn-Asn-Leu-Lys-Glu-Cys-Gly-Leu-Tyr-$CO_2^-$ (SEQ ID NO:1)

Peptide b ($G\alpha i_2$): $NH_2$-Lys-Asn-Asn-Leu-Lys-Asp-Cys-Gly-Leu-Phe-$CO_2^-$ (SEQ ID NO:31)

Peptide c3 ($G\alpha_t$): $NH_2$-Lys-Glu-Asn-Leu-Lys-Asp-Cys-Gly-Leu-Phe-$CO_2^-$ (SEQ ID NO:2)

Peptide d: $NH_2$-Lys-Asn-Asn-Leu-Lys-Glu-Ser-Gly-Leu-Tyr-$CO_2^-$ (SEQ ID NO:32)

The effect of solvation was explored only on peptide 1. This simulation was performed using the CHARMM molecular dynamics program. The simulations used 1 fs timesteps, the SHAKE constraints on bonds to hydrogen atoms, a dielectric constant of $\in=1$, and a 15 Å energy cutoff. The peptides were embedded in a 14 Å sphere of TIP3 water molecules, using stochastic boundary conditions. The water sphere was added in two steps, each of which involved overlaying a sphere of equilibrated water molecules at a random orientation followed by 20 ps of equilibration at 300 K. In this simulation 305 water molecules were added to the model in the first step, and 6 water molecules were added in the second step, resulting in a total of 311 water molecules. The total number of atoms in this simulation (peptide and water) was 1099 atoms.

Based on these computational methods, it was determined that peptides possessing anti-allergic activity share a cyclic conformation and that extended or linear conformations are inactive. Furthermore, analysis of the complex peptides show that the active species have a bend or turn at or near the junction of the importation competent segment and the anti-allergic segment.

Conformational measurements to confirm the computational analyses, based on NMR technologies and are performed as known in the art.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

References

Aridor M., Traub L. M. and Sagi-Eisenberg R. (1990). Exocytosis in mast cells by basic secretagogues: Evidence for direct activation of GTP-binding proteins. J. Cell Biol. 111:909–917.

Aridor M. and Sagi-Eisenberg R. (1990). Neomycin is a potent secretagogue of mast cells that directly activates a GTP-binding protein involved in. J. Cell Biol. 111:2885–2891.

Aridor M., Rajmilevich G., Beaven M. A. and Sagi-Eisenberg R. (1993). Activation of exocytosis by the heterotrimeric G protein $G_{i3}$. Science 262:1569–1572.

Bienenstock J., Tomioka M., Stead R., Ernst P., Jordana M., Gauldie J., Dolovich J. and Denburg J. (1987). Mast cell involvement in various inflammatory processes. Am. Rev. Respir. Dis. 135:S5–S8.

Chahdi A., Mousli M. and Landry Y. (1998). Substance P-related inhibitors of mast cell exocytosis act on G-proteins or on the cell surface. Eur. J. Pharmacol. 341,329–335.

Columbo M., Horowitz E. M., Kagey-Sobotka A. and Lichtenstein L. M. (1996). Substance P activates the release of histamine from human skin mast cells through a pertussis toxin-sensitive and protein kinase C-dependent mechanism. Clin. Immunol. Immunop. 81,68–73.

Devillier P., Regoli D., Asseraf A., Descours B., Marsac J. and Renoux M. (1986). Histamine release and local responses of rat and human skin to substance P and other mammalian tachykinins. Pharmacology 32:340–347.

Emadi-Khiav B., Mousli M., Bronner C. and Landry Y. (1995). Human and rat cutaneous mast cells: involvement of a G protein in the response to peptidergic stimuli. Eur. J. Pharmacol. 272,97–102.

Ennis M., Pearce F. L. and Weston P. M. (1980). Some studies on the release of histamine from mast cells stimulated with polylysine. Br. J. Pharmacol. 70:329–334.

Foreman J. C. (1987a). Neuropeptides and the pathogenesis of allergy. Allergy 42:1–11.

Foreman J. C. (1987b). Substance P and calcitonin gene-related peptide: Effect on mast cells and in human skin. Int. Archs. Allergy Appl. Immun. 82:366–371.

Goldberg A., Korzets Z., Bernheim J. And Mekori Y. A. (1991). Cutaneous responses to histamine, compound 48/80 and codeine in patients with chronic renal failure. Annals Allergy 67 :525–528.

Gomperts B. D., Churcher Y., Koffer A., Lillie T. H. W., Tatham P. E. R. and Whalley T. D (1991). Intracellular mechanisms regulating exocytotic secretion in mast cells. Int. Arch. Allergy Appl. Immunol. 94:38–46.

Hawiger J. 1997. Cellular import of functional peptides to block intracellular signaling. Curr. Opin. Immunol. 9: 189–194.

Kivity S., Sneh E., Greif J., Topilsky M. and Mekori Y. A. (1988). The effect of food and exercise on the skin response to compound 48/80 in patients with food-associated exercise-induced utricaria-angioedema. J. Allergy Clin. Immunol. 81:1155–1158.

Lichtenstein L. M (1993). Allergy and the immune system. Scientific American 269: 116–124.

Lin Y. Z., Yau S. Y., Veach R. A., Torgerson T. R and Hawiger J. (1995). Inhibition of nuclear translocation of transcription factor NF-kB by a synthetic peptide containing a cell membrane-permeable motif and nuclear localization sequence. J. Biol. Chem. 270:14255–14258.

Liu X. Y., Timmons S., Lin Y. Z. and Hawiger J. (1996). Identification of a functionally important sequence in the cytoplasmic tail of integrin β3 by using cell-permeable peptide analogs. Proc, Natl. Acad. Sci. 93:11819–11824.

Mousli M., Hugli T. E. Landry Y. and Bronner C. (1994). Peptidergic pathway in human skin and rat peritoneal mast cell activation. Immunopharmacol. 27:1–11.

Pearce F. L., Kassessinoff T. A., Liu W. L. (1989). Characteristics of histamine secretion induced by neuropeptides: Implications for the relevance of peptide-mast cell interactions in allergy and inflammation. Int. Arch. Allergy Appl. Immunol. 88:129–131.

Prochiantz A. (1996). Getting hydrophilic compounds into cells: lessons from homeopeptides. Curr. Opin. Neurobiol. 6:629–634.

Rojas M., Yau S. Y. and Lin Y. Z.(1996). Controlling epidermal growth factor (EGF)-stimulated Ras activation in intact cells by a cell-permeable peptide mimicking phosphorylated EGF receptor. J Biol. Chem. 271,27456–27461.

Sagi-Eisenberg R. (1993). Signal-transmission pathways in mast cell exocytosis. In: Immunopharmacology of mast cells and Basophils.

Sagi-Eisenberg R., Ben-Neriah Z., Pecht I., Terry S. and Blumberg S. (1983). Structure-activity relationship in the mast cell degranulation capacity of neurotensin fragments. Neuropharm. 22:197–201.

Shefler I., Taube Z., Medalia O. and Sagi-Eisenberg R. (1998). Basic secretagogues activate protein tyrosine phosphorylation and release of arachidonic acid in mast cells via a novel protein kinase C and phosphatidylinositol 3-kinase-dependent mechanism. Eur. J. Immunol. 28:3468–3478.

Sussman G. L., Harvey R. P. and Schocket A. L (1982). Evaluation of skin test response using two techniques of measurement. Ann. Allergy 48:75–77.

Theoharides T. C. (1996). The mast cell: a neuroimmunoendocrine master player. Int. J. Tissue React. 18:1–21.

What is claimed is:

1. An anti-allergic agent, comprising a complex molecule having at least a first segment competent for importation of said molecule into mast cells, and a second segment for having an anti-allergic effect with said mast cells, said first segment being a peptide and joined to said second segment through a linker, said linker providing a bend or turn at or near the junction between the two segments, with the proviso that the first segment is other than the peptide AAVALLPAVLLALLAP (SEQ ID NO: 27), when the second segment is the anti-allergic decapeptide of the C-terminal end of Gαi3 (SEQ ID NO: 1) or Gαt (SEQ ID NO: 2), wherein said first segment comprises 10–50 amino acids having a hydrophobic, lipid soluble portion.

2. The agent of claim 1, wherein said second segment has said anti-allergic effect by at least significantly reducing degranulation of said mast cells.

3. The agent of claim 2, wherein said second segment is selected from the group consisting of a peptide, a peptidomimetic, or a polypeptide.

4. The agent of claim 3, wherein said second segment is a peptide, having a cyclic conformation stabilized by bonds selected from the group consisting of hydrogen bonds, ionic bonds and covalent bonds.

5. The agent of claim 4, wherein said first segment is a peptide.

6. The agent of claim 5, wherein said linker is a covalent bond.

7. The agent of claim 6, wherein said covalent bond is a peptide bond.

8. The agent of claim 6, wherein said anti-allergic segment has an amino acid sequence selected from the group consisting of:

a decapeptide derived from Gαi$_3$ having the sequence KNNLKECGLY (SEQ ID NO:1);

a decapeptide derived from Gαt having the sequence KENLKDCGLF (SEQ ID NO:2);

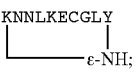

(SEQ ID NO: 3)

KNNLKECGL-para-amino-F (SEQ ID NO:4); KQNLKECGLY (SEQ ID NO:5);

KSNLKECGLY (SEQ ID NO:6); KNNLKEVGLY (SEQ ID NO:7); and

KENLKECGLY (SEQ ID NO:8).

9. The agent of claim 7, wherein the anti-allergic segment is a peptide taken from the C terminal sequence of Gαi₃.

10. The agent of claim 7, wherein said molecule is a peptide having an amino acid sequence selected from the group consisting of
WALL006: AAVALLPAVLLALLAPKQNLKECGLY (SEQ ID NO: 11)
WALL007: AAVALLPAVLLALLAPKNNLKEVGLY (SEQ ID NO: 12)
WALL008: Succinyl-AAVALLPAVLLALLA-Sar-KNNLKECGLY (SEQ ID NO: 13)
WALL010: VTVLALGALAGVGVGPKNNLKECGLY (SEQ ID NO: 15)
WALL011: Succinyl-AAVALLPAVLLALLAPKSNLKECGLY (SEQ ID NO: 16)
WALL012: Succinyl-AAVALLPAVLLALLAPKENLKECGLY (SEQ ID NO: 17)
WALL013: Succinyl-AAVALLPAVLLALLAPKANLKECGLY (SEQ ID NO: 18)
WALL014: Succinyl-AAVALLPAVLLALLAPKNNLKECGL-para-amino-F (SEQ ID NO: 19)
WALL015: Succinyl-AAVALLPAVLLALLAPKQNLKECGLY (SEQ ID NO: 20)
WALL016: Succinyl-AAVALLPAVLLALLAPKNNLKEVGLY (SEQ ID NO: 21).

11. A pharmaceutical composition for treating an allergic condition in a subject, comprising a therapeutically effective amount of an anti-allergic agent, said anti-allergic agent comprising a complex molecule having at least a first segment competent for importation of said molecule into mast cells, and a second segment for having an anti-allergic effect within said mast cells, said first segment being a peptide and joined to said second segment through a linker, said linker providing a bend or turn at or near the junction between the two segments, with the proviso that the first segment is other than the peptide AAVALLPAVLLALLAP (SEQ ID NO: 27), when the second segment is the anti-allergic decapeptide of the C-terminal end of Gαi3 (SEQ ID NO: 1) or Gαt (SEQ ID NO: 2), wherein said first segment comprises 10–50 amino acids having a hydrophobic, lipid soluble portion.

12. The composition of claim 11, wherein the allergic condition is selected from the group consisting of nasal allergy, an allergic reaction in an eye of the subject, an allergic reactions in the skin of the subject, acute urticaria, psoriasis, psychogenic or allergic asthma, interstitial cystitis, bowel diseases, migraines, and multiple sclerosis.

13. The composition of claim 11 further comprising a pharmaceutically acceptable excipient, diluent or carrier.

14. The composition of claim 13, wherein said composition is suitable for topical administration.

15. The composition of claim 14, wherein said topical administration is to the skin of the subject.

16. The composition of claim 13, wherein said composition is suitable for administration intranasally or by inhalation.

17. The composition of claim 11, wherein said second segment has said anti-allergic effect by at least significantly reducing degranulation of said mast cells.

18. The composition of claim 17, wherein said second segment is selected from the group consisting of a peptide, a peptidomimetic, or a polypeptide.

19. The composition of claim 18, wherein said second segment is a peptide, having a cyclic conformation, stabilized by bonds selected from the group consisting of hydrogen bonds, ionic bonds and covalent bonds.

20. The composition of claim 19, wherein said first segment is a peptide.

21. The composition of claim 20, wherein said linker is a covalent bond.

22. The composition of claim 21, wherein said covalent bond is peptide bond.

23. The composition of claim 21, wherein said anti-allergic segment has an amino acid sequence selected from the group consisting of
a decapeptide derived from Gαi₃ having the sequence KNNLKECGLY (SEQ ID NO:1);
a decapeptide derived from Gαt having the sequence KENLKDCGLF (SEQ ID NO:2);

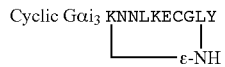

(SEQ ID NO: 3)

KNNLKECGL-para-amino-F (SEQ ID NO:4); KQNLKECGLY (SEQ ID NO:5);
KSNLKECGLY (SEQ ID NO:6); KNNLKEVGLY (SEQ ID NO:7); and
KENLKECGLY (SEQ ID NO:8).

24. The composition of claim 21, wherein the anti-allergic segment is a peptide taken from the C terminal sequence of Gαi₃.

25. The composition of claim 21, wherein said molecule is a peptide having an amino acid sequence selected from the group consisting of
WALL006: AAVALLPAVLLALLAPKQNLKECGLY (SEQ ID NO: 11)
WALL007: AAVALLPAVLLALLAPKNNLKEVGLY (SEQ ID NO: 12)
WALL008: Succinyl-AAVALLPAVLLALLA-Sar-KNNLKECGLY (SEQ ID NO: 13)
WALL010: VTVLALGALAGVGVGPKNNLKECGLY (SEQ ID NO: 15)
WALL011: Succinyl-AAVALLPAVLLALLAPKSNLKECGLY (SEQ ID NO: 16)
WALL012: Succinyl-AAVALLPAVLLALLAPKENLKECGLY (SEQ ID NO: 17)
WALL013: Succinyl-AAVALLPAVLLALLAPKANLKECGLY (SEQ ID NO: 18)
WALL014: Succinyl-AAVALLPAVLLALLAPKNNLKECGL-para-amino-F (SEQ ID NO: 19)
WALL015: Succinyl-AAVALLPAVLLALLAPKQNLKECGLY (SEQ ID NO: 20)
WALL016: Succinyl-AAVALLPAVLLALLAPKNNLKEVGLY (SEQ ID NO: 21).

26. A method for treating an allergic condition in a subject, comprising the step of administering a therapeutically effective amount of the anti-allergic agent of claim 1 to the subject.

27. The method of claim 26, wherein the allergic condition is selected from the group consisting of nasal allergy, an allergic reaction in an eye of the subject, an allergic reactions in the skin of the subject, acute urticaria, psoriasis, psychogenic asthma, allergic asthma, interstitial cystitis, bowel diseases, migraines, and multiple sclerosis.

28. The method of claim 27, wherein the step of administering said anti-allergic agent is performed by topical administration.

29. The method of claim 28, wherein said topical administration is to the skin or the eye of the subject.

30. The method of claim 27, wherein the step of administering said anti-allergic agent is performed by inhalation or intranasal administration.

31. The method of claim 27, wherein the second segment of the anti-allergic agent has said anti-allergic effect by at least significantly reducing degranulation of said mast cells.

32. The method of claim 31, wherein said second segment is selected from the group consisting of a peptide, a peptidomimetic or a polypeptide.

33. The method of claim 32, wherein said second segment is a peptide having a cyclic conformation stabilized by bonds selected from the group consisting of hydrogen bonds, ionic bonds or covalent bonds.

34. The method of claim 33, wherein the first segment of the anti-allergic agent is a peptide.

35. The method of claim 34, wherein the linker of the anti-allergic agent is a covalent bond.

36. The method of claim 35, wherein said covalent bond is a peptide bond.

37. The method of claim 35, wherein said anti-allergic second segment has an amino acid sequence selected from the group consisting of: a decapeptide derived from Gαi$_3$ having the sequence KNNLKECGLY (SEQ ID NO:1);

a decapeptide derived from Gαt having the sequence KENLKDCGLF (SEQ ID NO:2);

(SEQ ID NO: 3)

KNNLKECGL-para-amino-F (SEQ ID NO:4); KQNLKECGLY (SEQ ID NO:5);
KSNLKECGLY (SEQ ID NO:6); KNNLKEVGLY (SEQ ID NO:7); and
KENLKECGLY (SEQ ID NO:8).

38. The method of claim 36, wherein the anti-allergic segment is a peptide taken from the C terminal sequence of Gαi$_3$.

39. The method of claim 36, wherein the molecule of the anti-allergic agent is a peptide having an amino acid sequence selected from the group consisting of:
WALL006: AAVALLPAVLLALLAPKQNLKECGLY (SEQ ID NO: 11)

WALL007: AAVALLPAVLLALLAPKNNLKEVGLY (SEQ ID NO: 12)

WALL008: Succinyl-AAVALLPAVLLALLA-Sar-KNNLKECGLY (SEQ ID NO: 13)

WALL010: VTVLALGALAGVGVGPKNNLKECGLY (SEQ ID NO: 15)

WALL011: Succinyl-AAVALLPAVLLALLAPKSNLKECGLY (SEQ ID NO: 16)

WALL012: Succinyl-AAVALLPAVLLALLAPKENLKECGLY (SEQ ID NO: 17)

WALL013: Succinyl-AAVALLPAVLLALLAPKANLKECGLY (SEQ ID NO: 18)

WALL014: Succinyl-AAVALLPAVLLALLAPKNNLKECGL-para-amino-F (SEQ ID NO: 19)

WALL015: Succinyl-AAVALLPAVLLALLAPKQNLKECGLY (SEQ ID NO: 20)

WALL016: Succinyl-AAVALLPAVLLALLAPKNNLKEVGLY (SEQ ID NO: 21).

and the active analogues, homologues and derivatives of the sequences, including cyclic derivatives.

40. A method for preventing late phase inflammatory responses induced by protein kinase activation, comprising the step of administering a therapeutically effective amount of the anti-allergic agent of claim 1 to the subject.

41. The method of claim 40 wherein the protein kinase activity is a mitogen activated protein kinase.

42. The method of claim 40 wherein the anti allergic agent is according to claim 1.

43. The method of claim 40 wherein the anti-allergic agent is Peptide 2, Peptide 2-Succ and Peptide 2-Cyc.

44. A method for promoting importation of an anti-allergic peptide into a cell of a subject in vivo, the method comprising the steps of:

(a) preparing the anti-allergic agent of claim 1 by attaching to the anti-allergic peptide a leader sequence, the leader sequence being a peptide, via a linker or a direct bond which forms a bend or turn, to form the complex molecule;

(b) administering the complex molecule to the subject; and (c) importing the complex molecule into the cell through the leader sequence, such that the anti-allergic is imported into the cell.

* * * * *

SEQUENCE LISTING

```
<160> NUMBER OF SEQ ID NOS: 32

<210> SEQ ID NO 1
<211> LENGTH: 10
<212> TYPE: PRT
<213> ORGANISM: Artificial sequence
```

```
<220> FEATURE:
<223> OTHER INFORMATION: Decapeptide derived from Homo sapience
      G-alpha-i3

<400> SEQUENCE: 1

Lys Asn Asn Leu Lys Glu Cys Gly Leu Tyr
1               5                   10

<210> SEQ ID NO 2
<211> LENGTH: 10
<212> TYPE: PRT
<213> ORGANISM: Artificial sequence
<220> FEATURE:
<223> OTHER INFORMATION: Decapeptide derived from Homo sapience
      G-alpha-t

<400> SEQUENCE: 2

Lys Glu Asn Leu Lys Asp Cys Gly Leu Phe
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(10)
<223> OTHER INFORMATION: A bond exists between the side chain of K at
      position 1 and the c-terminus of the peptide

<400> SEQUENCE: 3

Lys Asn Asn Leu Lys Glu Cys Gly Leu Tyr
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: Para-amino Phenylalanine at position 10

<400> SEQUENCE: 4

Lys Asn Asn Leu Lys Glu Cys Gly Leu Phe
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Lys Gln Asn Leu Lys Glu Cys Gly Leu Tyr
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 6

Lys Ser Asn Leu Lys Glu Cys Gly Leu Tyr
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Lys Asn Asn Leu Lys Glu Val Gly Leu Tyr
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic peptide

<400> SEQUENCE: 8

Lys Glu Asn Leu Lys Glu Cys Gly Leu Tyr
1               5                   10

<210> SEQ ID NO 9
<211> LENGTH: 26
<212> TYPE: PRT
<213> ORGANISM: Artificial sequence
<220> FEATURE:
<223> OTHER INFORMATION: Synthetic peptide

<400> SEQUENCE: 9

Ala Ala Val Ala Leu Leu Pro Ala Val Leu Leu Ala Leu Leu Ala Ala
1               5                   10                  15

Lys Asn Asn Leu Lys Glu Cys Gly Leu Tyr
            20                  25

<210> SEQ ID NO 10
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (26)..(26)
<223> OTHER INFORMATION: Para-amino Phenylalanine at position 26

<400> SEQUENCE: 10

Ala Ala Val Ala Leu Leu Pro Ala Val Leu Leu Ala Leu Leu Ala Pro
1               5                   10                  15

Lys Asn Asn Leu Lys Glu Cys Gly Leu Phe
            20                  25

<210> SEQ ID NO 11
<211> LENGTH: 26
<212> TYPE: PRT
<213> ORGANISM: Artificial sequence
<220> FEATURE:
<223> OTHER INFORMATION: Synthetice peptide

<400> SEQUENCE: 11

Ala Ala Val Ala Leu Leu Pro Ala Val Leu Leu Ala Leu Leu Ala Pro
1               5                   10                  15
```

Lys Gln Asn Leu Lys Glu Cys Gly Leu Tyr
            20                  25

<210> SEQ ID NO 12
<211> LENGTH: 26
<212> TYPE: PRT
<213> ORGANISM: Artificial sequence
<220> FEATURE:
<223> OTHER INFORMATION: Synthetic peptide

<400> SEQUENCE: 12

Ala Ala Val Ala Leu Leu Pro Ala Val Leu Leu Ala Leu Leu Ala Pro
1               5                   10                  15

Lys Asn Asn Leu Lys Glu Val Gly Leu Tyr
            20                  25

<210> SEQ ID NO 13
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-terminal amino acid is succinylated
<220> FEATURE:
<221> NAME/KEY: MISC_FEATURE
<222> LOCATION: (16)..(16)
<223> OTHER INFORMATION: N-methyl amino acid

<400> SEQUENCE: 13

Ala Ala Val Ala Leu Leu Pro Ala Val Leu Leu Ala Leu Leu Ala Xaa
1               5                   10                  15

Lys Asn Asn Leu Lys Glu Cys Gly Leu Tyr
            20                  25

<210> SEQ ID NO 14
<211> LENGTH: 25
<212> TYPE: PRT
<213> ORGANISM: Artificial sequence
<220> FEATURE:
<223> OTHER INFORMATION: Synthetic peptide

<400> SEQUENCE: 14

Val Thr Val Leu Ala Leu Gly Ala Leu Ala Gly Val Gly Val Gly Lys
1               5                   10                  15

Asn Asn Leu Lys Glu Cys Gly Leu Tyr
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic peptide

<400> SEQUENCE: 15

Val Thr Val Leu Ala Leu Gly Ala Leu Ala Gly Val Gly Val Gly Pro
1               5                   10                  15

Lys Asn Asn Leu Lys Glu Cys Gly Leu Tyr
            20                  25

<210> SEQ ID NO 16
<211> LENGTH: 26

```
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 16

Ala Ala Val Ala Leu Leu Pro Ala Val Leu Leu Ala Leu Leu Ala Pro
1               5                   10                  15

Lys Ser Asn Leu Lys Glu Cys Gly Leu Tyr
            20                  25

<210> SEQ ID NO 17
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 17

Ala Ala Val Ala Leu Leu Pro Ala Val Leu Leu Ala Leu Leu Ala Pro
1               5                   10                  15

Lys Glu Asn Leu Lys Glu Cys Gly Leu Tyr
            20                  25

<210> SEQ ID NO 18
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 18

Ala Ala Val Ala Leu Leu Pro Ala Val Leu Leu Ala Leu Leu Ala Pro
1               5                   10                  15

Lys Ala Asn Leu Lys Glu Cys Gly Leu Tyr
            20                  25

<210> SEQ ID NO 19
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated
<220> FEATURE:
<221> NAME/KEY: MISC_FEATURE
<222> LOCATION: (26)..(26)
<223> OTHER INFORMATION: Para-amino Phenylalanine at position 26

<400> SEQUENCE: 19

Ala Ala Val Ala Leu Leu Pro Ala Val Leu Leu Ala Leu Leu Ala Pro
1               5                   10                  15

Lys Asn Asn Leu Lys Glu Cys Gly Leu Phe
```

-continued

```
<210> SEQ ID NO 20
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 20

Ala Ala Val Ala Leu Leu Pro Ala Val Leu Leu Ala Leu Leu Ala Pro
1               5                   10                  15

Lys Gln Asn Leu Lys Glu Cys Gly Leu Tyr
            20                  25

<210> SEQ ID NO 21
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 21

Ala Ala Val Ala Leu Leu Pro Ala Val Leu Leu Ala Leu Leu Ala Pro
1               5                   10                  15

Lys Asn Asn Leu Lys Glu Val Gly Leu Tyr
            20                  25

<210> SEQ ID NO 22
<211> LENGTH: 26
<212> TYPE: PRT
<213> ORGANISM: Artificial sequence
<220> FEATURE:
<223> OTHER INFORMATION: Synthetic peptide

<400> SEQUENCE: 22

Ala Ala Val Ala Leu Leu Pro Ala Val Leu Leu Ala Leu Leu Ala Pro
1               5                   10                  15

Tyr Leu Gly Cys Glu Lys Leu Asn Asn Lys
            20                  25

<210> SEQ ID NO 23
<211> LENGTH: 26
<212> TYPE: PRT
<213> ORGANISM: Artificial sequence
<220> FEATURE:
<223> OTHER INFORMATION: Synthetic peptide

<400> SEQUENCE: 23

Ala Ala Val Ala Leu Leu Pro Ala Val Leu Leu Ala Leu Leu Ala Pro
1               5                   10                  15

Lys Asn Asn Leu Lys Glu Cys Gly Leu Tyr
            20                  25

<210> SEQ ID NO 24
<211> LENGTH: 26
<212> TYPE: PRT
<213> ORGANISM: Artificial sequence
```

```
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: N-terminal amino acid is succinylated

<400> SEQUENCE: 24

Ala Ala Val Ala Leu Leu Pro Ala Val Leu Leu Ala Leu Leu Ala Pro
1               5                   10                  15

Lys Asn Asn Leu Lys Glu Cys Gly Leu Tyr
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic peptide

<400> SEQUENCE: 25

Ala Ala Val Ala Leu Leu Pro Ala Val Leu Leu Ala Leu Leu Ala Pro
1               5                   10                  15

Lys Glu Asn Leu Lys Asp Cys Gly Leu Phe
            20                  25

<210> SEQ ID NO 26
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (17)..(26)
<223> OTHER INFORMATION: A bond exists between the side chain of K at
      position 17 and the c-terminus of the peptide

<400> SEQUENCE: 26

Ala Ala Val Ala Leu Leu Pro Ala Val Leu Leu Ala Leu Leu Ala Pro
1               5                   10                  15

Lys Asn Asn Leu Lys Glu Cys Gly Leu Tyr
            20                  25

<210> SEQ ID NO 27
<211> LENGTH: 16
<212> TYPE: PRT
<213> ORGANISM: Homo sapiens

<400> SEQUENCE: 27

Ala Ala Val Ala Leu Leu Pro Ala Val Leu Leu Ala Leu Leu Ala Pro
1               5                   10                  15

<210> SEQ ID NO 28
<211> LENGTH: 15
<212> TYPE: PRT
<213> ORGANISM: Homo sapiens

<400> SEQUENCE: 28

Val Thr Val Leu Ala Leu Gly Ala Leu Ala Gly Val Gly Val Gly
1               5                   10                  15

<210> SEQ ID NO 29
<211> LENGTH: 26
<212> TYPE: PRT
<213> ORGANISM: Artificial sequence
```

```
<220> FEATURE:
<223> OTHER INFORMATION: Synthetic peptide

<400> SEQUENCE: 29

Ala Ala Val Ala Leu Leu Pro Ala Val Leu Leu Ala Leu Leu Ala Pro
1               5                   10                  15

Lys Asn Asn Leu Lys Glu Cys Gly Leu Tyr
            20                  25

<210> SEQ ID NO 30
<211> LENGTH: 26
<212> TYPE: PRT
<213> ORGANISM: Artificial sequence
<220> FEATURE:
<223> OTHER INFORMATION: Synthetic peptide

<400> SEQUENCE: 30

Ala Ala Val Ala Leu Leu Pro Ala Val Leu Leu Ala Leu Leu Ala Pro
1               5                   10                  15

Lys Asn Asn Leu Lys Glu Ser Gly Leu Tyr
            20                  25

<210> SEQ ID NO 31
<211> LENGTH: 10
<212> TYPE: PRT
<213> ORGANISM: Homo sapiens

<400> SEQUENCE: 31

Lys Asn Asn Leu Lys Asp Cys Gly Leu Phe
1               5                   10

<210> SEQ ID NO 32
<211> LENGTH: 10
<212> TYPE: PRT
<213> ORGANISM: Homo sapiens

<400> SEQUENCE: 32

Lys Asn Asn Leu Lys Glu Ser Gly Leu Tyr
1               5                   10
```